(12) United States Patent
Petros et al.

(10) Patent No.: US 12,370,341 B2
(45) Date of Patent: *Jul. 29, 2025

(54) PESSARY SYSTEM AND METHOD FOR PELVIC FLOOR LIGAMENT SUPPORT

(71) Applicant: Pamarope Pty Limited, Adelaide (AU)

(72) Inventors: Peter Emmanuel Petros, Elizabeth Bay (AU); Paul Andrew Zadow, Allenby Gardens (AU)

(73) Assignee: PAMAROPE PTY LIMITED, Adelaide (AU)

( * ) Notice: Subject to any disclaimer, the term of this patent is extended or adjusted under 35 U.S.C. 154(b) by 117 days.

This patent is subject to a terminal disclaimer.

(21) Appl. No.: 18/157,184

(22) Filed: Jan. 20, 2023

(65) Prior Publication Data
US 2023/0149661 A1    May 18, 2023

Related U.S. Application Data

(63) Continuation of application No. 17/651,410, filed on Feb. 16, 2022, now Pat. No. 11,602,613.
(Continued)

(51) Int. Cl.
*A61M 25/00* (2006.01)
*A61M 25/10* (2013.01)

(52) U.S. Cl.
CPC .. *A61M 25/0041* (2013.01); *A61M 25/10182* (2013.11); *A61M 25/10185* (2013.11);
(Continued)

(58) Field of Classification Search
CPC ........ A61M 25/0041; A61M 25/10182; A61M 25/10185; A61M 2025/1013;
(Continued)

(56) References Cited

U.S. PATENT DOCUMENTS

| | | |
|---|---|---|
| 3,646,929 A | 3/1972 | Bonnar |
| 4,198,981 A | 4/1980 | Sinnreich |

(Continued)

FOREIGN PATENT DOCUMENTS

| | | |
|---|---|---|
| EP | 0474906 | 3/1992 |
| WO | 1998/019606 A1 | 5/1998 |
| WO | 2020181103 A1 | 9/2020 |

OTHER PUBLICATIONS

Extended European Search Report for EP Application No. 22782377.0 , European Patent Office, Jan. 24, 2025.
(Continued)

*Primary Examiner* — Chelsea E Stinson
*Assistant Examiner* — Hamza A Darb
(74) *Attorney, Agent, or Firm* — GOTTLIEB, RACKMAN & REISMAN, P.C.

(57) ABSTRACT

A pessary system for providing pelvic floor support for USL and other ligaments. The pessary has an elongated probe with independently inflatable balloons each located substantially the same distance from the insertion end of the probe and which inflate into separate radial sectors. The probe can be inserted into a vaginal cavity and the balloons inflated provide mechanical support to the USLs. Independent inflation of each balloon allows the mechanical USL support provided to be varied on left and right sides to compensate for differences in the degree of degradation and positioning of the USL ligaments on either side.

19 Claims, 25 Drawing Sheets

Related U.S. Application Data

(60) Provisional application No. 63/168,784, filed on Mar. 31, 2021.

(52) U.S. Cl.
CPC ............... *A61M 2025/1013* (2013.01); *A61M 2205/054* (2013.01); *A61M 2210/1475* (2013.01); *A61M 2230/08* (2013.01)

(58) Field of Classification Search
CPC .... A61M 2205/054; A61M 2210/1475; A61M 2230/08; A61M 2025/0681; A61M 25/1011; A61M 2025/1081; A61M 2025/1084; A61M 25/1018; A61M 25/10181; A61M 2025/1061; A61M 31/00; A61M 2025/0004; A61M 25/10; A61M 25/007; A61B 2503/08; A61B 5/202; A61B 5/251; A61B 5/296; A61B 5/391; A61B 5/6847; A61B 5/6853; A61B 5/6867; A61B 5/6879; A61B 5/6885; A61N 1/0452; A61N 1/048; A61N 1/36007; A61N 1/36014; A61F 6/08
See application file for complete search history.

(56) References Cited

U.S. PATENT DOCUMENTS

| | | |
|---|---|---|
| 4,612,924 A | 9/1986 | Cimber |
| 4,693,704 A | 9/1987 | Ogita |
| 5,007,894 A | 4/1991 | Enhoming |
| 5,224,494 A | 7/1993 | Enhoming |
| 5,603,685 A | 2/1997 | Tutrone, Jr. |
| 5,611,768 A | 3/1997 | Tutrone, Jr. |
| 6,015,428 A | 1/2000 | Pagedas |
| 6,039,686 A | 3/2000 | Kovac |
| 6,050,937 A | 4/2000 | Benderev |
| 6,451,024 B1 | 9/2002 | Thompson et al. |
| 6,470,890 B1 | 10/2002 | Diokno et al. |
| 6,503,190 B1 | 1/2003 | Ulmsten et al. |
| 6,638,284 B1 | 10/2003 | Rousseau et al. |
| 6,645,137 B2 | 11/2003 | Ulmsten et al. |
| 6,753,372 B1 | 6/2004 | Garcia Duran et al. |
| 6,981,983 B1 | 1/2006 | Rosenblatt et al. |
| 8,401,650 B2 | 3/2013 | Simon et al. |
| 9,913,594 B2 | 3/2018 | Li et al. |
| 10,687,977 B1 * | 6/2020 | Hardart ................. A61F 6/08 |
| 11,602,613 B2 * | 3/2023 | Petros ................. A61B 5/391 |
| 2002/0161382 A1 | 10/2002 | Neisz et al. |
| 2003/0130669 A1 | 7/2003 | Damarati |
| 2005/0240211 A1 * | 10/2005 | Sporri ............... A61M 25/1002 |
| | | 606/193 |
| 2006/0276699 A1 * | 12/2006 | Komachi ............. A61B 5/0075 |
| | | 600/341 |
| 2011/0237876 A1 | 9/2011 | Browning |
| 2014/0083433 A1 | 3/2014 | Lowry |
| 2015/0032030 A1 | 1/2015 | Iglesias |
| 2016/0121087 A1 | 5/2016 | Ward et al. |
| 2020/0383703 A1 | 12/2020 | Atad et al. |

OTHER PUBLICATIONS

Petros et al, "An Integral Theory of Female Urinary Incontinence", Acta Obstet Gynecol Scand, 07/3111990, 69 Suppl. 153, pp. 7-31, 1990.

Petros et al., The Female Pelvic Floor: Function, Dysfunction and Management According to the Integral Theory, Feb. 25, 2010, Springer 3rd ed.

Coloplast, Altis Single Incision Sling System product brochure, "Predictability and Control for Female Stress Urinary Incontinence", Jun. 18, 2018.

Coloplast, Altis Single Incision Sling System Procedural Steps (2018).

International Search Report for PCT/US2022/070663 (WO2022212980) Mailing Date—Apr. 12, 2022.

Written Opinion for PCT/US2022/070663 (WO2022212980) Mailing Date—Apr. 12, 2022.

* cited by examiner

PESSARY SYSTEM AND METHOD FOR PELVIC FLOOR LIGAMENT SUPPORT

CROSS-REFERENCE TO RELATED APPLICATIONS

This application is a continuation of U.S. Patent Application Ser. No. 17/651,410 filed on Feb. 16, 2022, now U.S. Pat. No. 11,602,613B2, and which claims priority to U.S. Provisional Application Ser. No. 63/168,784 filed on Mar. 31, 2021, the entire contents of which is expressly incorporated by reference.

BACKGROUND

Urinary incontinence is a condition that effects many women, particularly in an aging population. The symptoms of "overactive bladder" include urination urge, frequent need to urinate, nocturia, and inability to empty properly. Up to 75% of female nursing home patients experience some degree of urinary incontinence. Various surgical and non-surgical treatments are used to treat this condition.

In surgical treatment techniques that are used to treat stress urinary incontinence, existing tissue can be coapted or mechanical structures implanted to provide support for internal organs. One particular treatment involves implanting a midurethral sling to provide support for the bladder and/or urethra. For example, U.S. Pat. No. 10,426,594 discloses anchoring a filamentary support element to tissues lateral to the urethra and implanting the filament into fascial tissue to provide a ligamentary support for the urethra between the first and second locations. The support allows existing musculature to better apply pressure to the urethra.

Because surgical solutions are not available for all such conditions, and also due to risk and cost, non-surgical techniques for managing female incontinence are frequently used. Such techniques include use of vaginal pessaries. Vaginal pessaries are removable devices designed to support pelvic organ prolapse, a condition where the bladder, rectum, or uterus drops down toward the vagina. Conventional vaginal pessaries used for prolapse prevention rely on placement of a pessary in the vaginal cavity to block the descent of a prolapsed organ, such as the bladder (cystocele), rectum (rectocele), or uterus (hysterocele) by acting as a barrier to descent of the prolapsed organ itself.

Pessaries can be designed for long term placement or temporary placement and removal. Long term placed configurations can cause ulceration, especially in older women. Accordingly, temporary pessaries are often preferred for this type of patient.

Pessaries are available in a variety of designs. Donut or ring type pessaries are designed to surround the cervix and provide a platform in the vagina to prevent descent. One example of an expandable pessary is disclosed in U.S. Pat. No. 6,645,137 to Ulmsten et al. Expandable pessaries are designed for placement in the vagina where they then are spread out to form a platform that acts as a mechanical blockage to the descending prolapse.

One type of expandable pessary is an inflatable pessary, such as shown in U.S. Pat. No. 6,470,890 to Diokno et al. A conventional inflatable pessary is designed to be inserted into the vagina in an uninflated state and positioned behind the pubic bone. The balloon portion is inflated to the desired amount, such as with air, water, or saline. When inflated, the balloon expands within a 360 degree area surrounding the pessary device to form a ball or cylinder shape around the pessary axis. The inflated balloon applies pressure to the surrounding areas in the vaginal cavity to support the prolapsed organ. Inflatable pessaries like this are also useful for treatment of stress incontinence because the inflated balloon creates pressure on the urethra to prevent urine from leaking out during normal activities.

Although conventional pessary designs can provide organ support and apply urethral pressure to relieve prolapse symptoms, they are not designed to address underlying causes of prolapses. In particular, bladder bowel and uterine prolapses, plus bladder bowel and chronic pelvic pain symptoms can be the result of loose or damaged ligaments. Deficiency in collagen, which is the main structural component of the ligaments, weakens the ligaments over time so they stretch down to cause prolapse. Because the pelvic muscles contract against the ligaments, the forces which close and open the bladder and bowel also weaken, resulting in various bladder, bowel and pain symptoms. (See, Petros PE & Ulmsten U., An Integral Theory Of Female Urinary Incontinence. *Acta Obstetricia et Gynecologica Scandinavica*, 1990; 69; Supp. 153: 1-79.)

Accordingly, there is a need for an improved vaginal pessary that provides targeted mechanical support to the uterosacral ligaments and other pelvic ligaments to treat prolapse and other conditions. It would be a further benefit to provide a pessary that can be used on a temporary basis and easily placed and removed by a medical practitioner and by the user. Yet a further benefit would be provided if such a pessary can be easily customized to provide support for multiple different ligamentary areas in the pelvis. Yet an additional benefit would be provided if such a pessary design could also be used as a platform for support and placement of sensors and electrodes, such as for use in EMG recording and muscle stimulation.

SUMMARY

These and other issues are addressed by an inflatable pessary system as disclosed herein and which is configured to provide specific mechanical support to loose pelvic floor ligaments to thereby support a prolapsed organ and/or relieve other pelvic floor symptoms. Depending on placement and configuration, ligamentary support can be provided to address prolapse of the bladder, bowel, and/or uterus. By mechanically supporting loose ligaments improved treatment of bladder, bowel, and pain symptoms resulting from prolapse and non-prolapse conditions related to loose ligaments is also provided.

In an embodiment, the pessary system comprises an elongated flexible probe configured for insertion into a vaginal cavity. Two inflatable balloon portions, which can be independently inflatable, are located towards the insertion end of the probe. The probe can be inserted into the vagina to position the balloon portions at the back of the vagina, behind the cervix in the apex. Each balloon can be inflated with air or liquid, such as by use of a syringe attached to a fluid conduit leading to the balloon. The balloons are positioned on the probe so that when inflated they expand laterally and generally opposite to each other. When the balloons are inflated, the lateral expansion applies pressure to specific areas of the vaginal wall creating expansion pockets in those areas of the vaginal wall, such as below the uterosacral ligament (USL), and provide mechanical support for that ligament from below. By providing targeted ligament support, in areas where there is ligament weakness, expansion of the vaginal wall in other areas surrounding the pessary can be limited, reducing or avoiding over distention of the vagina and thus reducing ulceration, pain and discomfort that such distension may cause.

Independent inflation of each balloon allows for an asymmetric differential expansion of one balloon relative to the other. This allows for the mechanical support provided for each USL to be independently varied to compensate for differences in the degree of degradation and positioning of the USL ligaments on either side. The balloons can be deflated and the probe easily removed on a periodic basis, e.g., to allow the vagina to revascularize and to avoid ulceration.

The lateral balloons can be formed directly on the surface of the probe. Alternatively, the balloons can be placed in an internal core area of the probe and the probe's core surrounded by an outer sleeve. The outer sleeve can be positioned to block inflation of some of the balloons while others are allowed to inflate. In an embodiment, apertures are formed in the outer sleeve and the sleeve can be positioned so the apertures expose selected balloons. When these balloons are inflated they can expand through the respective aperture and laterally away from the probe. The sleeve constrains inflation of other balloons that are covered by the sleeve Variations in the shape and size of the apertures may be used to provide additional control to the size, shape, and position of each balloon as it expands. In an embodiment where independent balloon inflation is not required, a single balloon can be provided in alignment with the apertures of the outer sleeve so that on inflation the balloon expands through each of the apertures while inflation of remaining portion of the balloon is constrained by the outer sleeve.

Multiple balloons can be provided laterally along the length of the probe core and the position of the sleeve or apertures on the outer sleeve chosen to select specific balloons that can be inflated to extend from the probe. Each laterally placed balloon can each be coupled to a separate conduit for providing inflation fluid so that they are all independently inflatable. Alternatively, some or all of the balloons, such as all the balloons on a given side of the probe, can be connected to a common fluid conduit.

In a particular implementation, a catheter-like tube with a closed end is configured with multiple weakened portions along its length, at which positions inflation will occur when fluid is injected into the tube. The tube is located within the pessary and is surrounded by the outer sleeve. The outer sleeve operates to allow inflation laterally outward from the probe substantially only where an aperture is located and constrains inflation in other areas. Multiple sleeves can be provided with differently placed apertures to allow for customization of the position of the inflatable balloons by use of an appropriate sleeve. Alternatively a blank sleeve can be provided along with suitable tools to allow a doctor to create apertures in the sleeve at the desired locations.

In addition to providing ligamentary support to the respective USLs, the lateral expansion of the balloons also functions to securely anchor the probe in place. This allows for the probe to be used for additional and/or alternative purposes. One or more sliding sleeves carrying auxiliary balloons can be fitted onto the probe and placed so that when the probe is inserted and anchored with the primary balloons, the auxiliary balloons on the sleeve can be inflated below other damaged or loose pelvic ligaments, including the pubourethral (PUL), arcus tendinous fascia pelvis (ATFP), cardinal (CL), and perineal body (PB), to provide support for such ligaments along with providing additional support for the USL ligaments. This ligamentary support allows for selective treatment of stress urinary incontinence, cystocele, low rectocele/descending perineal syndrome, as well as addressing bladder, bowel, and chronic pelvic pain symptoms.

Electrodes and/or sensors can be placed on the lateral balloons or other locations on the probe. These can be used to allow EMG recording, muscle stimulation, and for other purposes. The electrode and sensor wires can be outside of the probe or the probe configured so the connecting wires run within the probe.

The flexible probe can be configured with a very slim form factor, allowing it to be easily used by elderly women who typically have very narrow vaginal cavities. The probe can also be sufficiently long to facilitate the processes of insertion and removal, particularly self-insertion and removal. At least the distal (non-insertion) end of the probe can be sufficiently flexible to allow it to be folded to allow the portion of the probe external to the vagina to be held inside the woman's underwear. Measurement indicia, such as marks at 1 cm intervals, can be provided on the probe to allow easy determination of the insertion distance.

DESCRIPTION OF THE DRAWINGS

Further features and advantages of the pessary system and methods as disclosed herein, as well as structure and operation of various implementations of the invention, are disclosed in detail below with references to the accompanying drawings in which.

DETAILED DESCRIPTION

Figure 1:
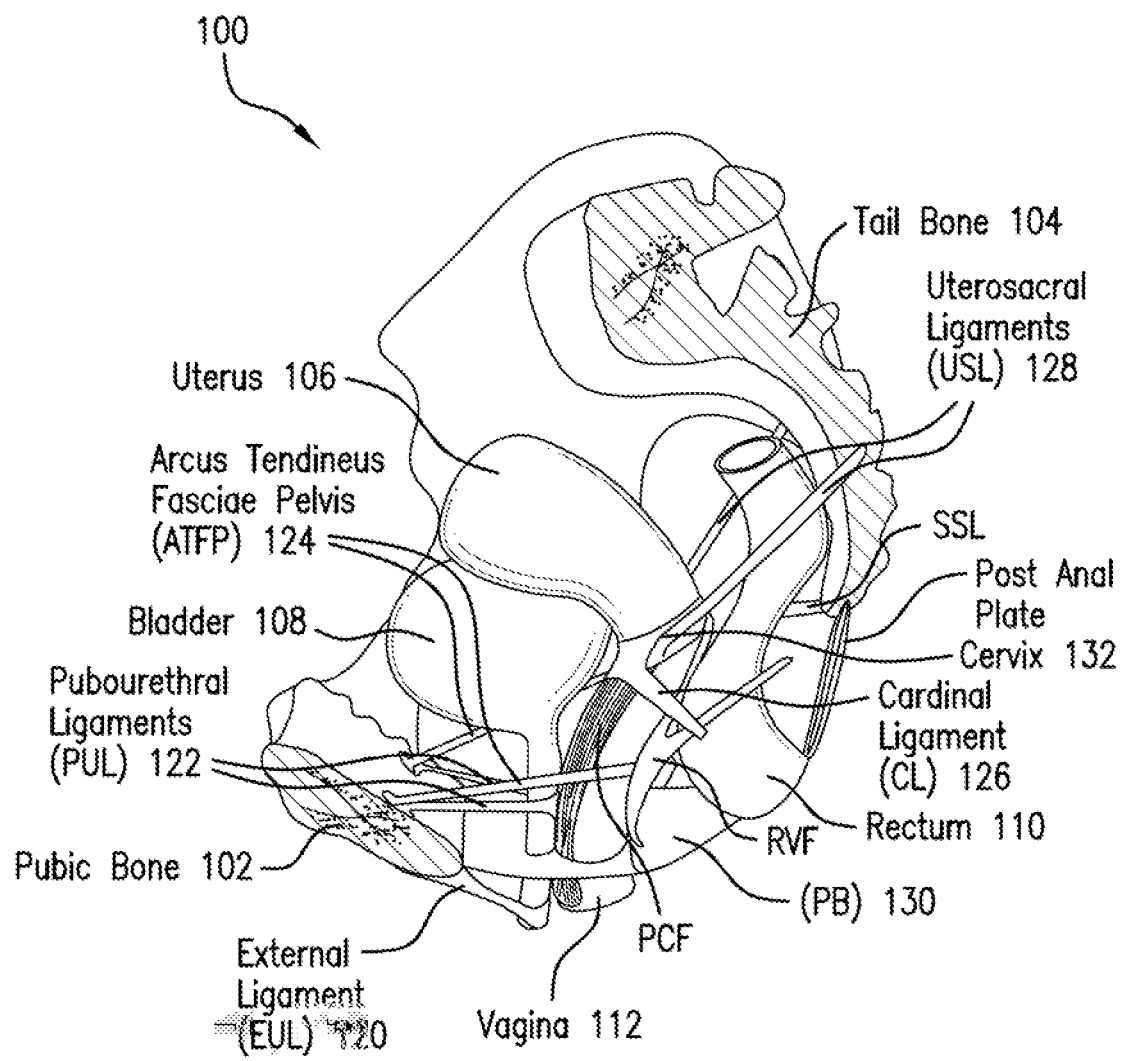
FIG. 1 is a diagram of relevant anatomy of a female pelvis 100 in medial cross para-sagittal section.

FIG. 1 is a diagram of relevant anatomy of a female pelvis 100 in medial cross section. Illustrated is the pubic bone 102 and tail bone 104. Situated between these bones is the uterus 106, bladder 108, rectum or bowel 110, and vagina 112. The five suspensory pelvic ligaments are also shown. These are the Pubourethral ligaments (PUL) 122, the Arcus Tendineus Fasciae Pelvis (ATFP), 124, the cardinal ligament (CL) 126, the uterosacral ligaments (USL) 128, and the perineal body (PB) 130. Also shown is the External Ligament (EUL) 120 and cervix 132, among other features.

It has been theorized that looseness or damage to one or more of these ligaments, such as may result from collagen deficiency or other mechanisms, is the cause of bladder, bowel, and uterine prolapses, plus bladder, bowel, and chronic pelvic pain symptoms. For example, a weakening of the ligament supporting an organ can result in stretching of the ligament downward resulting in organ prolapse. Because the pelvic muscles contract against the ligaments, the forces that close and open the bladder and bowel also weaken, resulting in specific bladder, bowel, and pain symptoms. The relationship between symptoms and ligament weakness is believed to be exponential such that even a minor prolapse can cause major symptoms. (See, Petros PE, THE FEMALE PELVIC FLOOR: Function, Dysfunction and Management, According to the Integral Theory, $3^{rd}$ ED 2010 *Springer Heidelberg*.)

Figure 2:
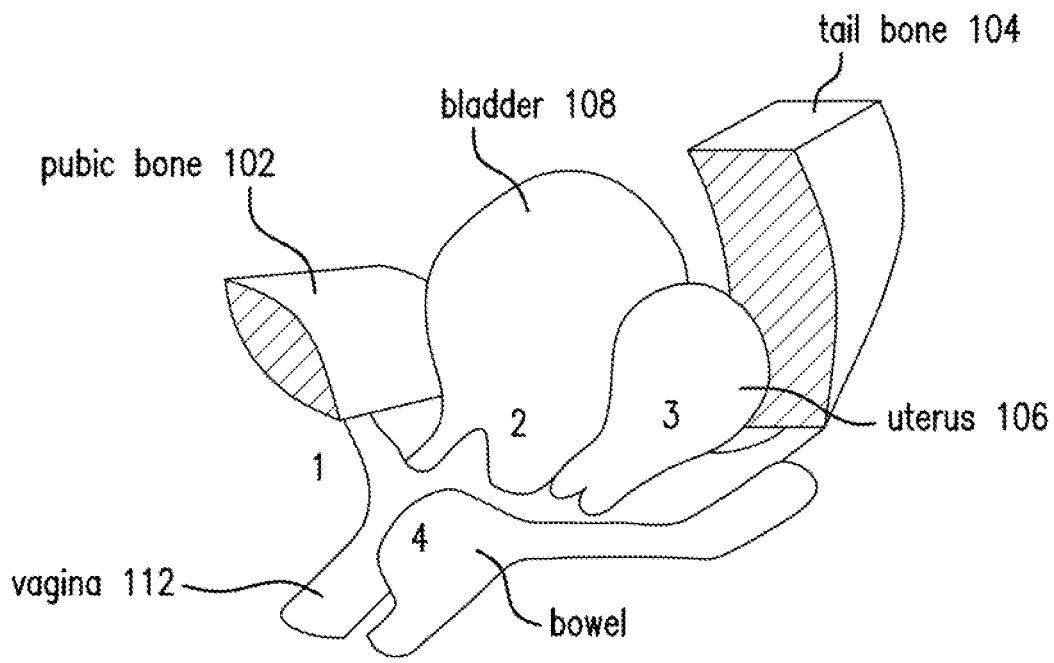
FIG. 2 is a table summarizing the association between symptoms and ligaments further identifying the impacted organ(s)

FIG. 2 is a diagram and chart summarizing the association between symptoms and particular ligaments and further identifying the impacted organ(s). Ligaments are divided into three zones: a front zone including the PUL ligaments, a middle zone, including the AFTF and CL ligaments, and a back or posterior zone, including the USL and PB ligaments. The thickness of the horizontal bar in the chart indicates a relative degree of association with the ligament at issue according to the Integral Theory.

With reference to FIG. 2, ligament weakness in the anterior zone (front ligaments) can result in stress urinary incontinence (SUI) but also bladder frequency, urgency, and fecal incontinence when associated with SUI. Ligament weakness in the middle zone (middle ligaments) can result in cystocele prolapse with associated symptoms of emptying, urgency, and chronic bladder infections. Ligament weakness in the posterior zone (back ligaments), including the USL ligaments, can result in uterine prolapse, apical if there has been a hysterectomy, enterocele, and high rectocele when the USLs are laterally separated. Associated symptoms of USL laxity include abnormal emptying of bladder and bowel, urgency to go to the toilet, inability to evacuate (bladder and bowel), nocturia, frequent need to evacuate, and chronic pelvic pain.

Figure 3A:
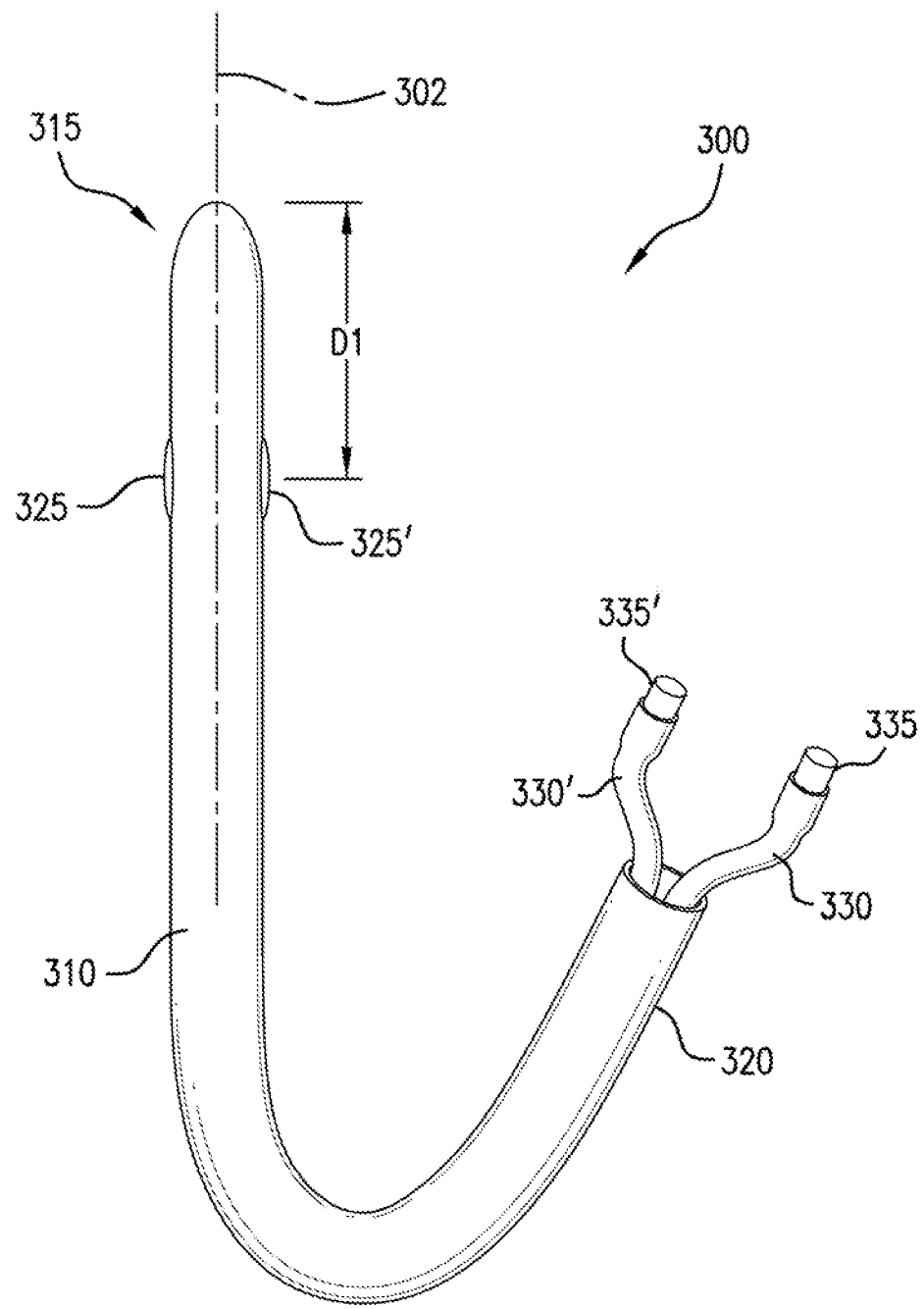
FIGS. 3A and 3B are illustrations of the basic features of a pessary according to an embodiment in an uninflated and inflated state respectively.
Figure 3B:
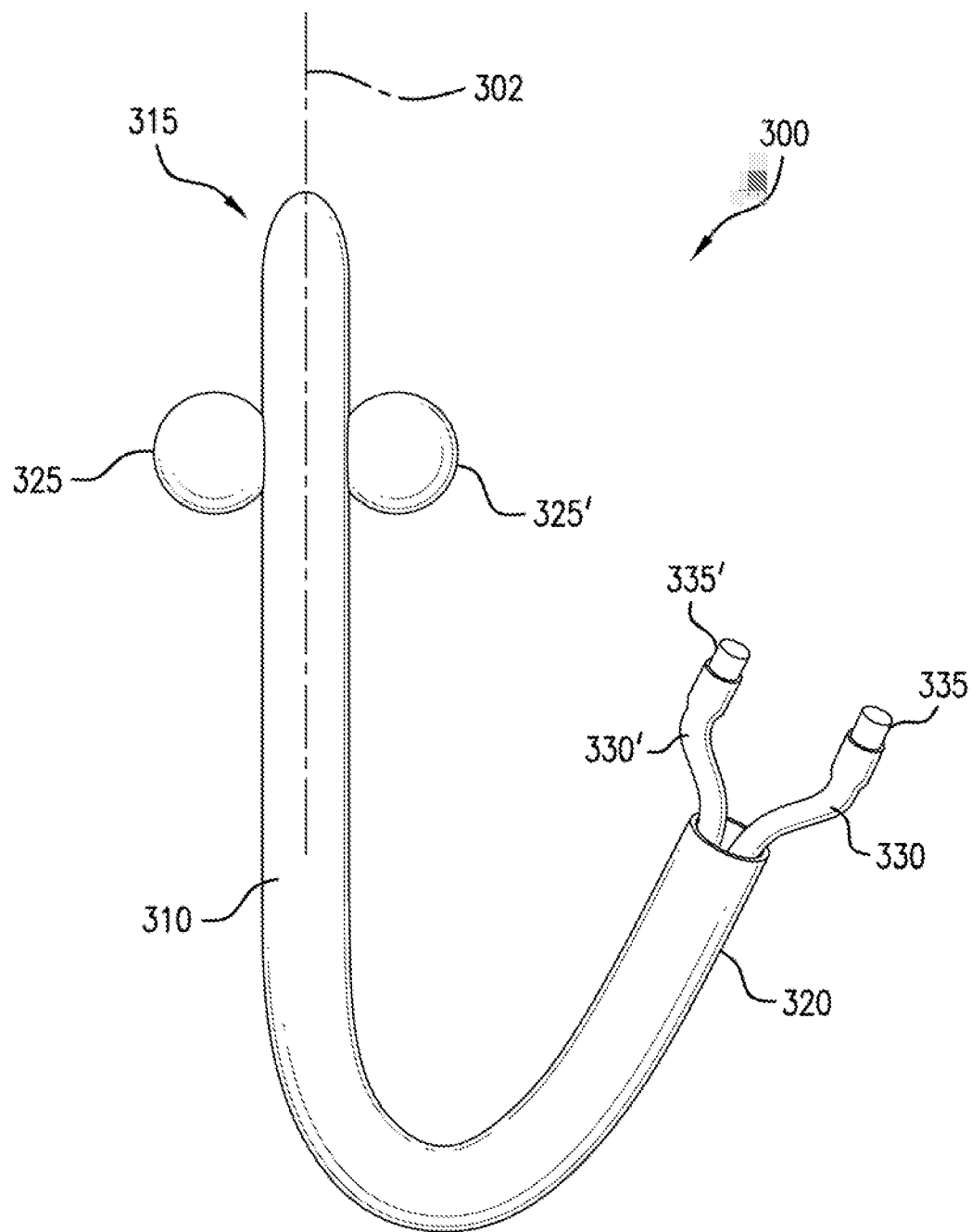

FIGS. 3A and 3B are illustrations of the basic features of an improved pessary 300 according to an embodiment and which can provide controllable mechanical support targeting uterosacral ligaments to thereby reduce symptoms and pain associated with or without bladder, bowel, and uterine prolapses. FIG. 3A shows the pessary 300 in an uninflated state and FIG. 3B shows pessary 300 of FIG. 3A in an inflated state.

Turning to FIGS. 3A and 3B, the pessary 300 comprises elongated flexible probe 310 that extends along a longitudinal axis 302. The probe 310 can be made of rubber, silicon rubber, or other flexible material that is biocompatible and safe for internal use. Suitable materials are known to those of skill in the art. The probe 310 is configured for insertion into a vaginal cavity and has an insertion end 315 and a distal end 320. The probe 310 has first and second inflatable portions 325, 325'. Each inflatable portion 325, 325' (alternatively referred to as a balloon) is a predefined distance, such as D1, from the insertion end 302. Each inflatable portion 325, 325' is in fluid communication with a respective fluid conduit 330, 330'.

In this embodiment, balloons 325, 325' are independently inflatable using fluid, such as air, water, or saline, introduced into the respective conduit 330, 330'. Independent inflation allows the balloons 325, 325' to be inflated to different degrees. Such differential expansion advantageously allows the pessary 300 to provide more precise mechanical support for respective ligaments, such as the USL, where one ligament is generally located more lateral than the other. In addition, differential inflation allows compensation for differential elasticity in the back part of vagina by allowing the distension from the inflatable portions 325, 325' to expand the vagina asynchronously. This reduces the possibility of excessive one-sided pressure that can ulcerate the vaginal wall. In an alternative embodiment, the lateral balloons may be coupled to the same fluid source and inflate together.

Various ways to provide fluid and inflate portions 325, 325' can be used. In one embodiment, a syringe (not shown) is connected to a respective conduit 330, 330' via a valved luer lock or other coupler 335, 335'. Other appropriate couplers 335, 335' are known to those of skill in the art. The amount inflatable portions 325, 325' expand is dependent on the design of the inflatable portions and the amount of injected fluid. For example, in a particular embodiment, the balloons can be independently inflated with up to 5 ml or up to 10 ml of liquid each. Of course, different inflation amounts may be used depending on the size of the balloons and the degree of desired inflation.

Figure 10A:
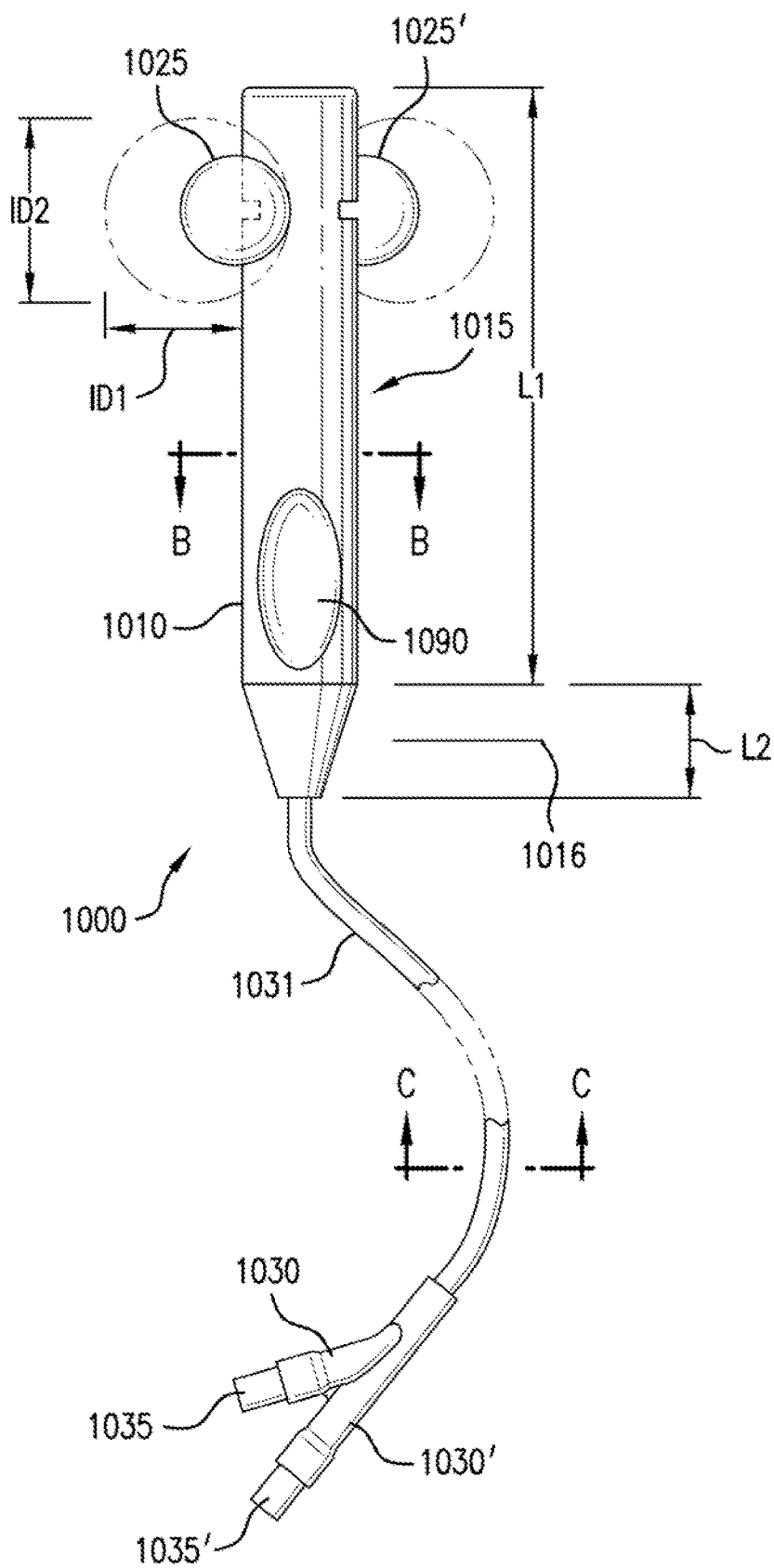
FIGS. 10A-10C show a particular embodiment of the pessary as in FIGS. 3A and 3B.
Figure 10B:
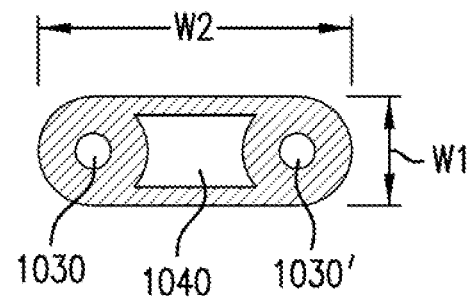
Figure 10C:
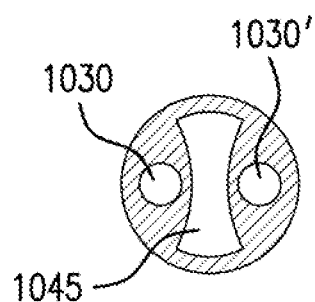

The fluid conduits 330, 330' can be physically separate tubes and may be surrounded in whole or part by an outer casing, such as larger tube through which conduit tubes pass. Conduits 330, 330' can be formed as channels that are integrally formed within a single tube. A combination of separate conduit tubes and integrated conduits may be used as well. Such as outer casing or tube with integral conduits may have the same or different width as the probe 310. For example, the casing may have a smaller diameter than the pessary probe. A particular embodiment with the fluid conduits integrally formed within a tube is shown in FIGS. 10A-10C discussed below.

The probe has a length L from the insertion end 315 to the distal end 320 and which is long enough to allow for full insertion of the probe 310 into a vaginal cavity and proper placement. In an embodiment, a portion of the probe remains external to allow for manipulation. A probe designed for insertion and removal by a third party, such as a doctor or nurse, may be shorter than one designed for self-insertion and removal. For example, the length L can be between 20 cm and 60 cm, between 30 cm and 50 cm and about 40 cm long or greater. In a particular embodiment, the pessary 300 has a length L sufficient so that when fully inserted into the vagina, a sufficient length of probe remains outside of the vagina to allow for a doctor to easily manipulate the position of the probe. For example, after insertion to the appropriate position the portion of the probe 310 outside of the vagina can be longer than the portion inside of the vagina. Pessary 300 can be configured so that the end portion 320 can be cut to adjust the length, after which couplers 335, 335' may need to be connected to cut ends of the fluid conduits 330, 330'. In a further embodiment, the pessary length L is selected so that only a small portion or even none of the pessary probe 310 remains external after insertion. The ends of the inflation conduits may remain external and provide a grasping means to extract the pessary.

The probe has a width W which can be relatively small to thereby provide a slim probe configuration allowing the pessary probe 310 to easily enter into the vagina even in the oldest woman with the narrowest vagina. Such a slim form factor is especially useful where the probe is for use in treatment of bladder and bowel problems in the frail women who inhabit nursing homes, 75% of whom have major bladder/bowel symptoms. In a particular configuration the probe 310 can have a width of between 1.5 cm and 1.6 cm. Other widths are also possible. For example the width W can be between 1.3 cm and 1.7 cm and between 1 cm and 2 cm. The probe can be fabricated with even narrower or wider widths, although wider widths may be more difficult to insert for certain patients.

The cross-sectional shape of the probe can be any suitable shape, including round, oblong or rounded rectangular. The cross-sectional shape may be selected to accommodate supplemental sleeves with auxiliary "blow up" balloons, discussed further below, allowing the sleeves to slide onto the probe and be manually positioned laterally while restricting axial rotation of such sleeves. The cross-sectional shape may also be selected to assist with placement orientation of the pessary probe for a woman to easily self-insert.

The probe width and shape does not need to be constant along the entire length of the probe 310. For example, the width of the probe 310 in the portion intended for vaginal insertion may be narrower than the portion intended to remain external or visa versa. In another embodiment, the vaginal insertion portion may be wider than the external portion. Thus, the insertion end could have a width within one of the ranges range noted above while the distal end is be larger to allow for easier manipulation of the probe and attachment of inflation syringes. Similarly, the cross-sectional shape may be different in different locations along the length of the sleeve. For example, the insertion end may have a round cross section to provide for easy insertion while the distal end has another shape, such as generally oblong, rectangular, triangular, or trapezoidal, and which allows the internal orientation of the probe to be easily determined by feel at or near the distal end.

A long pessary configuration, such as one with length of 40 cm or greater, facilitates the process of inserting and removal of the probe, filling and emptying the lateral balloons with fluid, with differential volumes for each if required. As noted, the probe 310 can be flexible along its length. The degree of flexibility may vary along the length of the probe 310, such as based on internal structures. The flexibility of the probe 310, allows a woman to easy self-insert and inflate the pessary 300. In a particular embodiment where more than a minimal a portion of the pessary remains external to the vagina after full insertion, such as more than 1 cm to 2 cm, the external portion is flexible enough so it can be bent and held in whole or part inside the woman's underwear during use. As noted above, in a configuration where the pessary probe is fully or substantially internal, portions, such as fluid conduit(s) used for inflation may extend a further distance. The conduits can be made of a conventional flexible tubing wherein this portion of the pessary can be bent to remain within the woman's underwear.

Figure 3C:
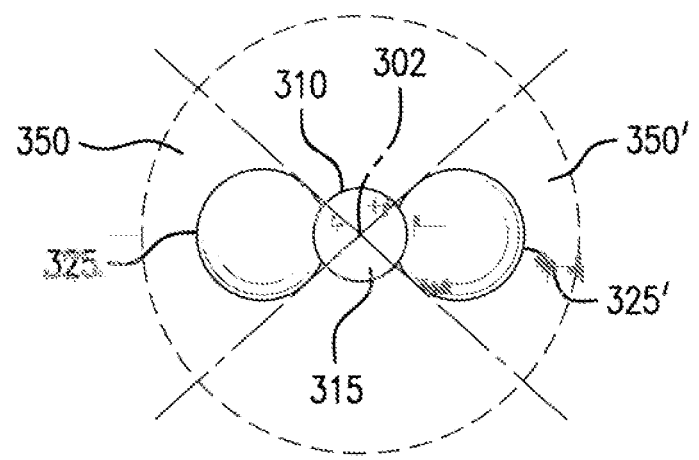
FIG. 3C shows the inflated pessary of FIG. 3B as viewed from the insertion end along the probe longitudinal axis.

FIG. 3C shows the inflated pessary 300 of FIG. 3B as viewed from the insertion end 315 along the longitudinal axis 302. As illustrated in FIG. 3C, in this embodiment each inflatable portion 325, 325' expands laterally outwards from the probe 310 when inflated. With consideration to a circular area centered on and normal to the longitudinal axis 302, the first inflatable portion 325 inflates into a first radial sector 350 relative to the longitudinal axis 302 of the probe 310. The second inflatable portion 325' when inflates into a second radial sector 350' relative to the longitudinal axis 302. The width of each sector is dependent on the geometry and maximum inflated size of the inflatable portions 325, 325'. The specific angular placement and width of the sectors can be selected with consideration of the anatomical location of the ligaments to be supported relative to the vaginal wall.

Figure 4:
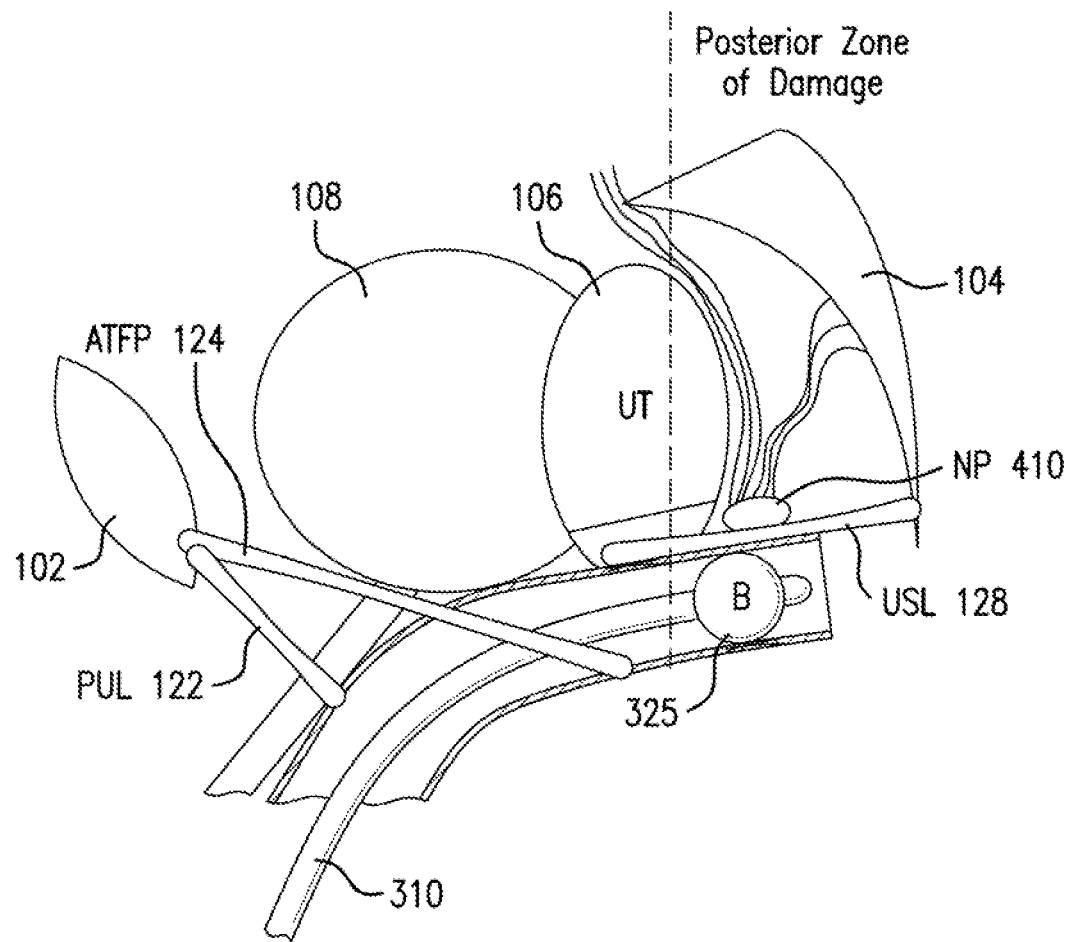
FIG. 4 is a diagram of a pessary as in FIGS. 3A-3C positioned for support of the USL and nerve plexuses.

Placement of the pessary 300 is discussed with respect to FIG. 4 which shows a pessary 300 positioned for support of the USL. The probe 310 of the pessary 300 is inserted into the vagina until the inflatable areas 325, 325' are in the back part of the vagina behind the cervix and the uterus 106. As the inflatable areas 325, 325' are inflated, they expand laterally as discussed above, pressing against the vaginal wall and creating expansion pockets in those areas. These pockets, as maintained by the balloons, provide ligamentary support.

In a particular configuration, the lateral position of the balloons is selected so that they each expand to position the expanded pockets of the vaginal wall below the uterosacral ligaments (USL) 128. By supporting the USLs, the pessary 300 can be used to help prevent uterine prolapse.

Also shown in FIG. 4 is nerve plexus (NP) 410 is anatomically supported by the USL 128, one on each side. NP 410 represents the sympathetic (T11-L2) and parasympathetic sacral (s2-4) situated about 2 cm from the insertion point of the USLs as they enter the lateral part of the cervix. Use of the pessary 300 puts the inflatable portions 325, 325' in the region of the NP 410. Sagging of the NP 410 can cause the nerves to fire and produce chronic pelvic pain which is then referred to the target point of specific nerve fibres (vagina=vulvodynia; bladder=interstitial cystitis; lower abdomen=dragging abdominal pain; sacral area=coccydynia; paraurethral="muscle spasm" and so on). The inflated balloons provide support for the NP 410 to prevent or reduce sagging of NP to alleviate associated pelvic pain, such as the pains listed above.

The probe 310 also mechanically reinforces the USLs to provide a firm anchoring point for the backward/downward directional muscle forces which stretch the vagina to provide underlying support for the bladder base and anorectal stretch receptors. If the bladder base and anorectal stretch receptors are unsupported, this may result in premature activation of the micturition and defecation reflexes which are perceived by the patient as bladder/bowel "urge incontinence" and a night "nocturia". In addition, the same ligaments anchor the muscles which stretch open the urethra and anorectum to facilitate evacuation of urine and feces. This is perceived as urinary retention and constipation.

As noted, different lateral expansion of the balloons can be used to provide targeted support of different structures. Turning to FIGS. 3D-3H, lateral placement for use in supporting different structures is discussed below with reference to a 12-hour clock face with the longitudinal axis 302 in the center of the face, with the 12:00 point dorsally oriented and the clock face generally sagittal oriented. While a sector is defined by a maximum design inflation, an inflatable portion that is not fully inflated does not need to fill its expansion sector. Thus, an inflatable portion with an expansion sector from 9:30-11:30 could when inflated to a desired amount a fill just the 10:00-11:00 sector. Inflatable portion 325, 325' can also be sized and positioned to provide combinations of ligamentary support.

Figure 3D:
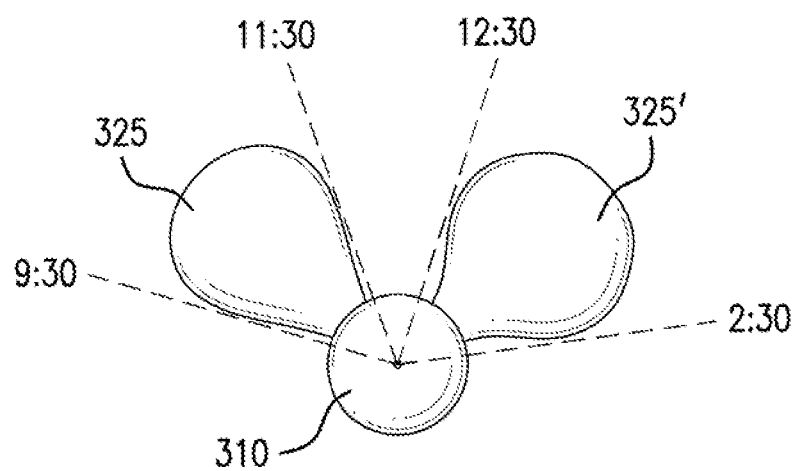
FIGS. 3D-3H illustrate different configurations of the pessary balloons for use in providing different types of support.
Figure 3E:
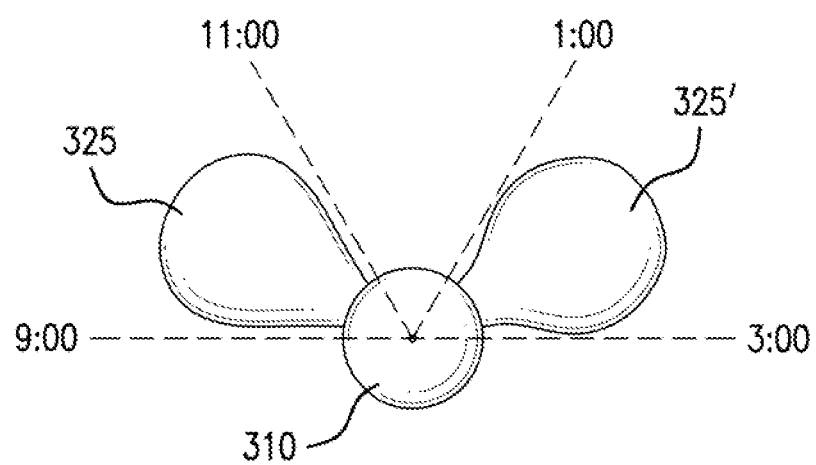
Figure 3F:
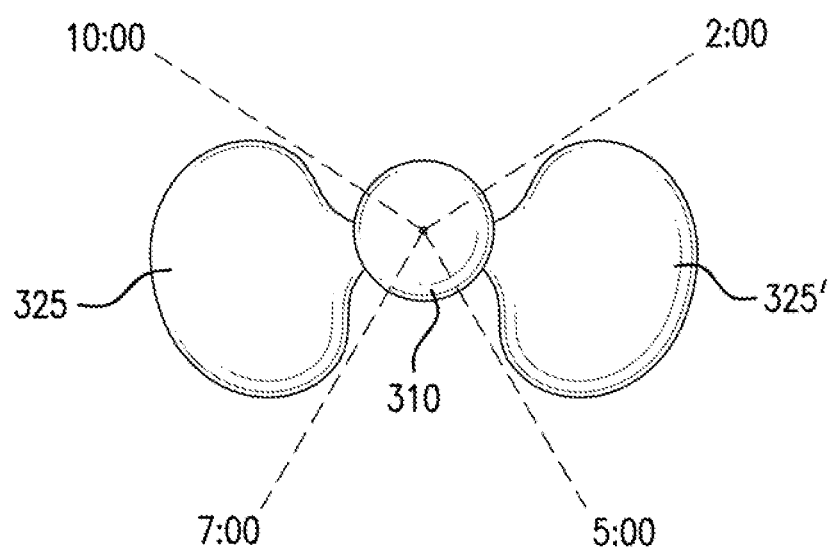
Figure 3G:
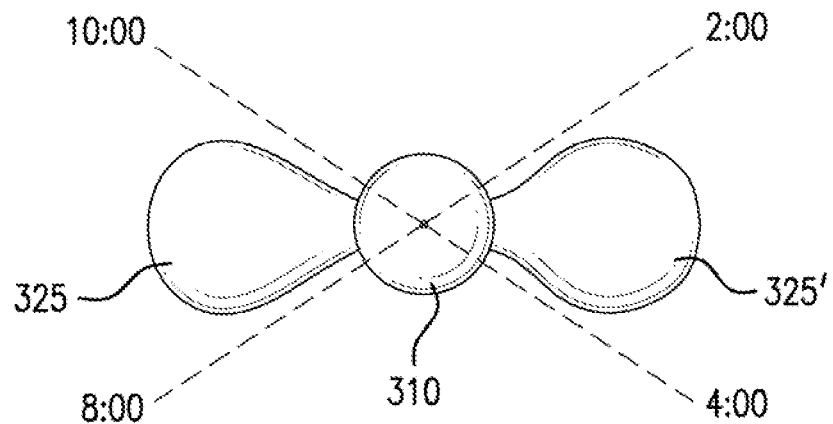
Figure 3H:
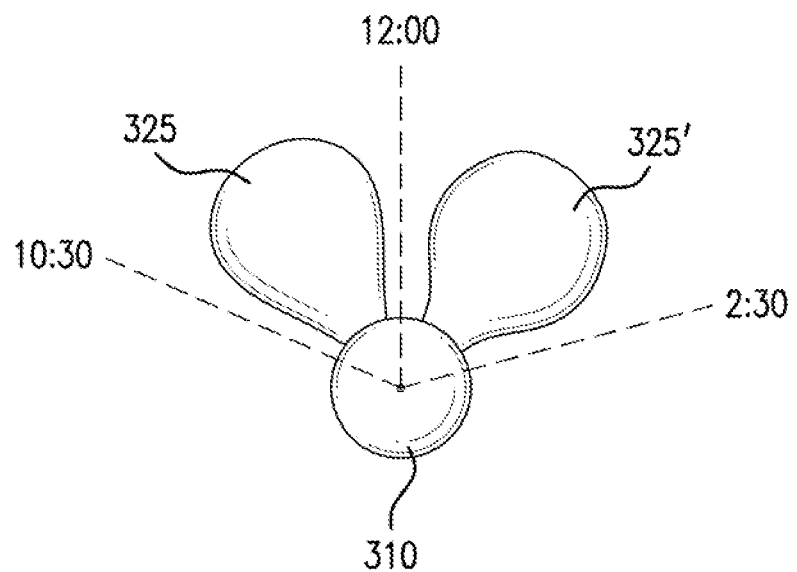

FIG. 3D illustrates balloons 325, 325' positioned to expand (when the pessary is inserted and positioned as appropriate) against the anterior vaginal wall with expansion sectors between 9:30-11:30 and 12:30-2:30 respectively to provide support to pubo urethral ligament at mid urethra with support balloons to each side of urethra. FIG. 3E illustrates balloons positioned to expand against the anterior vaginal wall behind the pubic bone with expansion sectors between 9:00-11:00 and 1-3:00 that extend posteriorly to provide support to the Arcus Tendinous Fascia Pelvis and insertion points of the levator muscles. FIG. 3F illustrates balloons positioned to expand against the posterior vaginal wall about 1-3 cm from the vagina introitus with expansion sectors from 7:00-10:00 and 2:00-5:00 to provide support for the deep transversus perinei ligament. FIG. 3G illustrates balloons positioned to expand against the anterior vaginal wall in the region of the anterior surface of the cervix with expansion sectors from 8:00-10:00 and 2:00-4:00 to provide support to the Cardinal Ligament (e.g., to treat high cystocoele or transverse defect). FIG. 3H illustrates balloons positioned to expand against the anterior vaginal wall posteriorly behind the cervix with expansion sectors from 9:30-12:00 and 12:00-2:30 to provide support for the insertion points on the Utero sacral ligament.

In the embodiments above, the expansion sectors are spaced apart from each other such that balloons filling the sector will not touch when fully inflated. In a further embodiment, the balloons 325, 325' can be positioned so that the expansion sectors are adjacent and wherein inflated balloons can touch. This embodiment may be useful, for example, to create a combined pocket in the vaginal wall that provides continuous support from one sector to the next, and where the independent inflation of the balloons allows for adjustment of the degree of support provided on each side of the combined sector. (See FIG. 3H) In general, the sectors will be adjacent or spaced apart but will not overlap. However, in an alternative embodiment, inflatable portions 325, 325' could be shaped and placed so that there is least some overlap. The relative position of the expansion sectors 350, 350' to each other can be specified by an angle between the midline of each sector. For example, the sectors can be positioned so sector midlines are between 90 and 180 degrees apart, or between 120 and 180 degrees apart where the sectors are at least generally opposite to each other, or at substantially 180 degrees apart resulting in sectors that are substantially opposite each other. It should be appreciated that the position of each sector can also be defined with other references, such as with respect to a +/−angle of rotation from the sagittal plane of the probe.

In sum, both the angle between each of the sectors and the angular width of each sector can be defined to position the balloons to provide the desired ligament support while limiting pressure on the vaginal wall in other areas around the pessary where support is not needed.

To allow for proper placement of the inflatable portions 325, 325' within the vagina, the distance D1 from the insertion end 315 of the probe to the inflatable portions can be selected to be the expected distance from the back of the vagina to the desired placement position of inflatable portions 325, 325' behind the uterus. Fully inserting the probe 310 will put the inflatable portions 325, 325' in the correct position. Alternatively, distance D1 can be less than the expected distance from the desired position of the inflatable portions 325, 325' and the back of the vagina. The probe 310 can have indicia marking distance intervals, such as at 1 cm intervals, and this marking can be used to gauge when the probe has been inserted the correct amount and to help gauge orientation to place the inflatable portions 325, 325' as desired, such as behind the uterus and to the side of the USLs 128. The proper insertion distance can be determined during a medical exam and communicated to the patient for reference during later self-insertion. Other techniques are also possible. For example, a doctor may fit a given pessary 300 to a patient and then add an indicia to the probe 310 to indicate the proper length to be inserted. In addition, as discussed further below with respect to FIGS. 8A-8D and FIG. 9, a pessary system can be provided in which the distance from the insertion end to the lateral inflatable portions is configurable so that when the pessary probe is fully inserted, the inflatable portions are in the proper location for the specific patient so as to provide USL or other support.

Advantageously, a pessary 300 as disclosed herein can be used intermittently and be easily self-inserted. For example a woman can self-insert and inflate the pessary 300 for use during the day and then easily deflate and remove it at night. This allows the vaginal tissue to rest and be revascularized, significantly reducing the propensity for ulceration. The pessary 300 can be used when going out to a social occasion but removed when the patient is at home. If used for nocturia, the pessary 300 can be removed for intercourse, and reinserted afterwards so as to control nocturia through the night. If used to control symptoms such as chronic pelvic pain, which can cyclically vary from mild to very severe, sometimes in the space of a few days, the pessary 300 can be inserted only when the pain is cyclically severe. It can also be inserted to assist in passing urine and then removed afterwards.

FIG. 10A is specific embodiment 1000 of the pessary 300 discussed above. Pessary 1010 has a probe body 1010 with first and second inflatable portions 1025, 1025'. The inflatable portions 1025, 1025' are fed by respective conduits 1030, 1030' which pass through a tube 1031 and into the probe body 1010. An indentation 1090 or other tactile element on one side of the probe body 1010 lets a person holding the probe easily determine the probe's orientation. Element 1090 can also be configured to allow for a more secure grip on the probe body 1010 during insertion and removal. The conduits 1030, 1030' can be terminated with valved luer locks 1035, 1035'. One conduit can extend further than the other and/or jut out at an angle to provide a clear indication of which conduit feeds which inflatable portion.

FIG. 10B is an illustration of a cross section of probe body 1010 along line B-B. The probe 1010 in this embodiment has a flattened shape with a thickness W1 and a width W2 that is greater than W1, such as between 1.5 and 2.5 times greater. The conduits 1035, 1035' are integrally formed within at least a portion the probe body 1010, such as by molding the probe body 1010 around separate conduit tubes or through an extrusion process. A central area 1040 of the probe body 1010 can be hollow to form a void. Having such a void can increase the flexibility of the probe for a given fabrication material and also reduce weight.

FIG. 10C is an illustration of a cross section of tube 1031 along line C-C. Similarly, and with reference to FIG. 10C, conduits 1030, 1030' can be integrally formed within at least a portion of the tube 1031. A central area 1045 of the tube 1031 can be hollow.

In one embodiment, the hollow void 1040 in the probe body is closed off so that the internal air or other fluid is trapped within. Likewise hollow void 1045 can be closed or open and may be connected to or separate from void 1040. In a variation, pessary 1000 can be configured so that air or other fluid can be selectively introduced to the void 1040, such as through an auxiliary valve (not shown). Adjusting the pressure of air in the void 1040 can increase or decrease the stiffness of the probe body 1010. In an exemplary embodiment, the probe body 1010 has a thickness W1 of about 5 mm and a width W2 of about 10 mm.

FIG. 10A shows the inflatable portions 1025, 1025' in a partially inflated state and shows a maximum inflation state in dotted line. Inflatable portions can be configured to inflate to an inflation diameter ID1 perpendicular to the probe axis of between 21 mm and 30 mm and a diameter ID2 measured along an axis parallel to the main axis of the probe of between 21 mm and 30 mm. The probe body can be provided in one or more lengths. For example, the forward portion 1015 of the probe body 1010 can be offered with a length L1 of between 80 mm and 90 mm, such as 85 mm, or a length of between 90 mm and 100 mm, such as 93 mm or 95 mm. A rear portion 1016 of the probe body is tapered with length L2. In an exemplary embodiment, L2 is between 5 mm and 10 mm, such as 7 mm. An outer diameter of tube 1031 can be between 3 and 5 mm, such as 4 mm or 4.2 mm. The channels 1030, 1030' can each have a diameter between 0.5 mm and 1.0 mm, such as 0.8 mm.

Figure 5A:
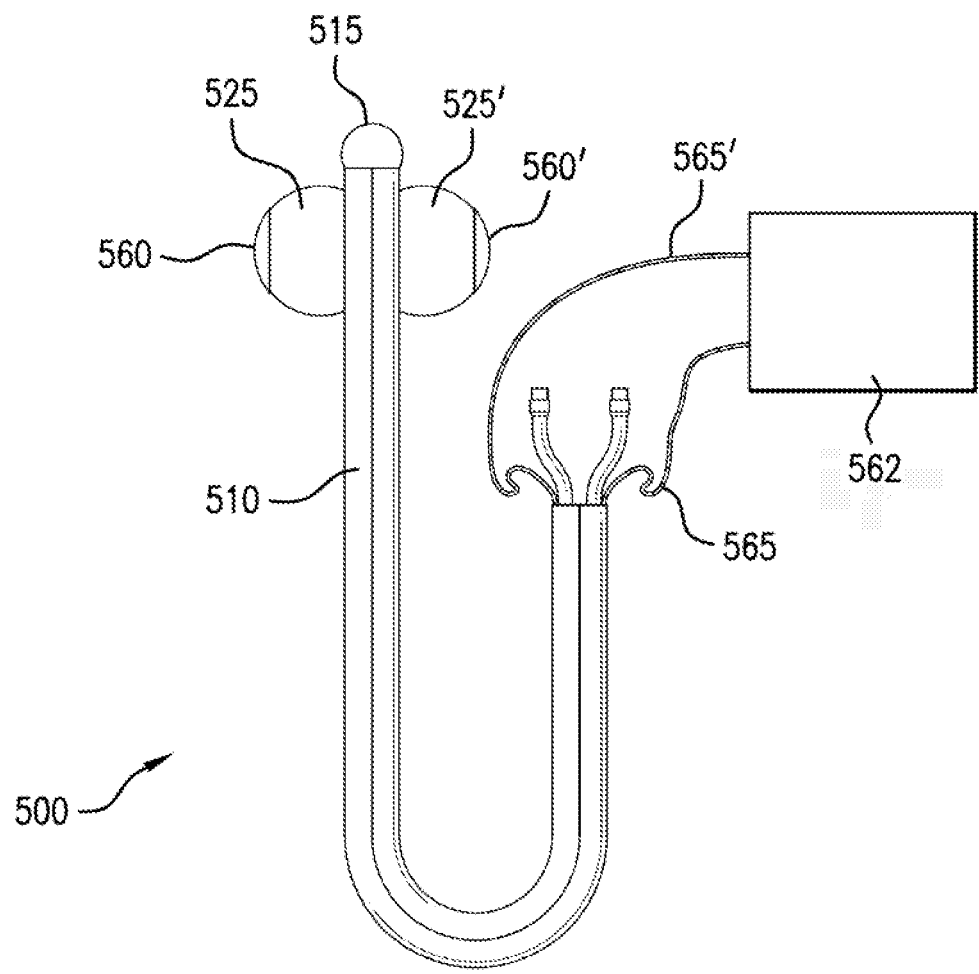
FIG. 5A shows an embodiment of a pessary 500 configured for electromyography assessment and muscle stimulation.

FIG. 5A shows a further embodiment of a pessary 500 configured for electromyography (EMG) assessment and muscle stimulation. Pessary 500 is similar to pessary 300 shown in FIGS. 3A-3C, above, and includes a probe portion 510 with an insertion end 515 and laterally positioned inflatable portions 525, 525'. In this embodiment, one or both of the inflatable portions 525, 525' can include electrodes, such as electrodes 560, 560'. Electrodes 560, 560' can be used as electrical sensors and/or sites for applying electrical stimulation to surrounding tissue. Wires 565, 565' electrically connect the electrode 560, 560' to appropriate circuitry 562, such as an EMG sensing signal display and/or analysis system, a muscle stimulation device, or other circuitry as desired. While only one electrode 560, 560' is shown on each inflatable portion 525, 525', more than one electrode can be present. For example, each inflatable portion 525, 525' could have two electrodes, one for EMG sensing of electrical activity in surrounding muscle tissue and one for stimulating surrounding muscle tissue. Other equipment, such as a pressure sensor, could also be mounted on an inflatable portion 525, 525'. Such inflatable portions 525, 525' in a pessary 500 used for EMG assessment and stimulation may be more robust than similar inflatable portions 325, 325' in pessary 300 as discussed above.

Figure 5B:
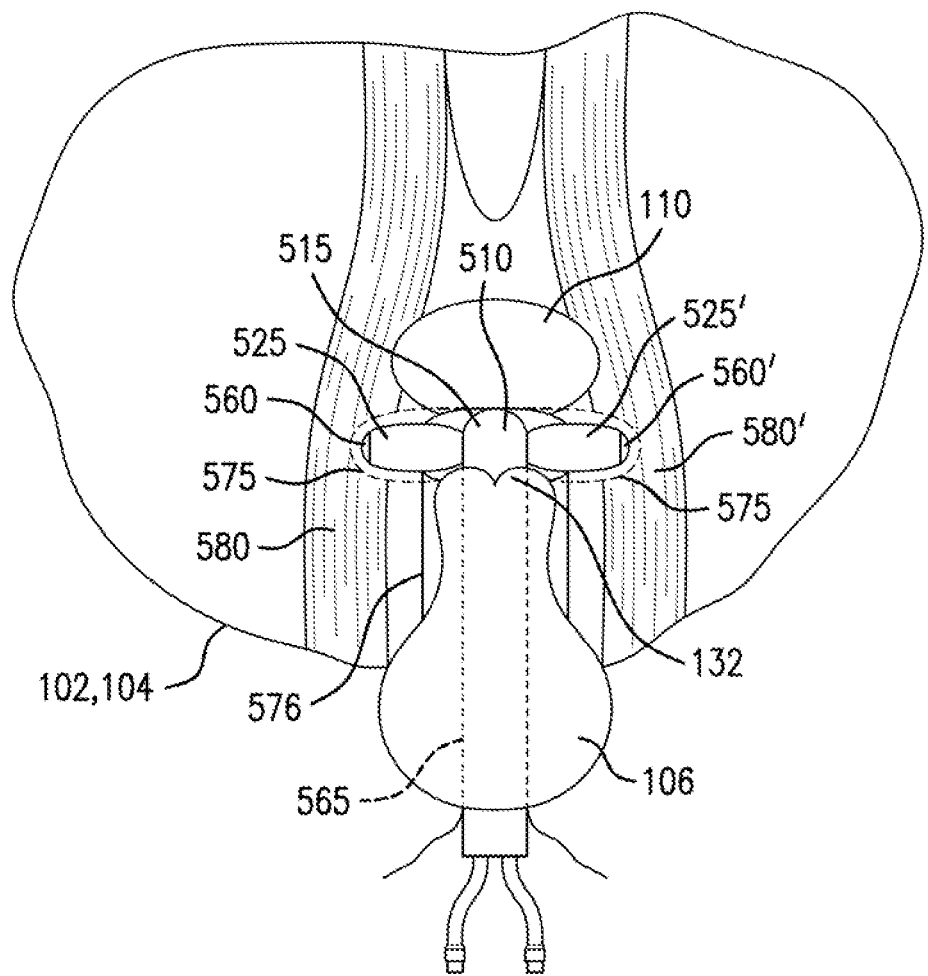
FIG. 5B is a diagram of the pessary of FIG. 5A in place and inflated for use in electromyography assessment and muscle stimulation.

In use, the inflatable portions 525, 525' carrying the EMG electrodes are inflated, e.g. with air, and expand laterally. With the pessary appropriately positioned, this expansion brings the EMG electrodes directly over the pelvic muscles on each side, such as the pubococcygeus muscles. The expanded balloons sit securely over the muscles while electrical recording or stimulation occurs. FIG. 5B shows a pessary 500 of FIG. 5A, inserted and with the inflatable portions 525, 525' expanded. These laterally expand the elastic vaginal wall 575 (situated past the lateral vaginal wall 576) to position the EMG electrodes 560, 560' adjacent the puboccygeus muscles 580, 580'.

The electrodes 560, 560' can be integrally formed with the inflatable portion 525, 525' during manufacture. Alternatively, the electrodes 560, 560' can be separately mounted onto the inflatable portions 525, 525', either during manufacture or at the time of use. The wires 565, 565' connected to electrodes 560, 560' can be routed within the probe 510 or along its exterior.

Figure 5C:
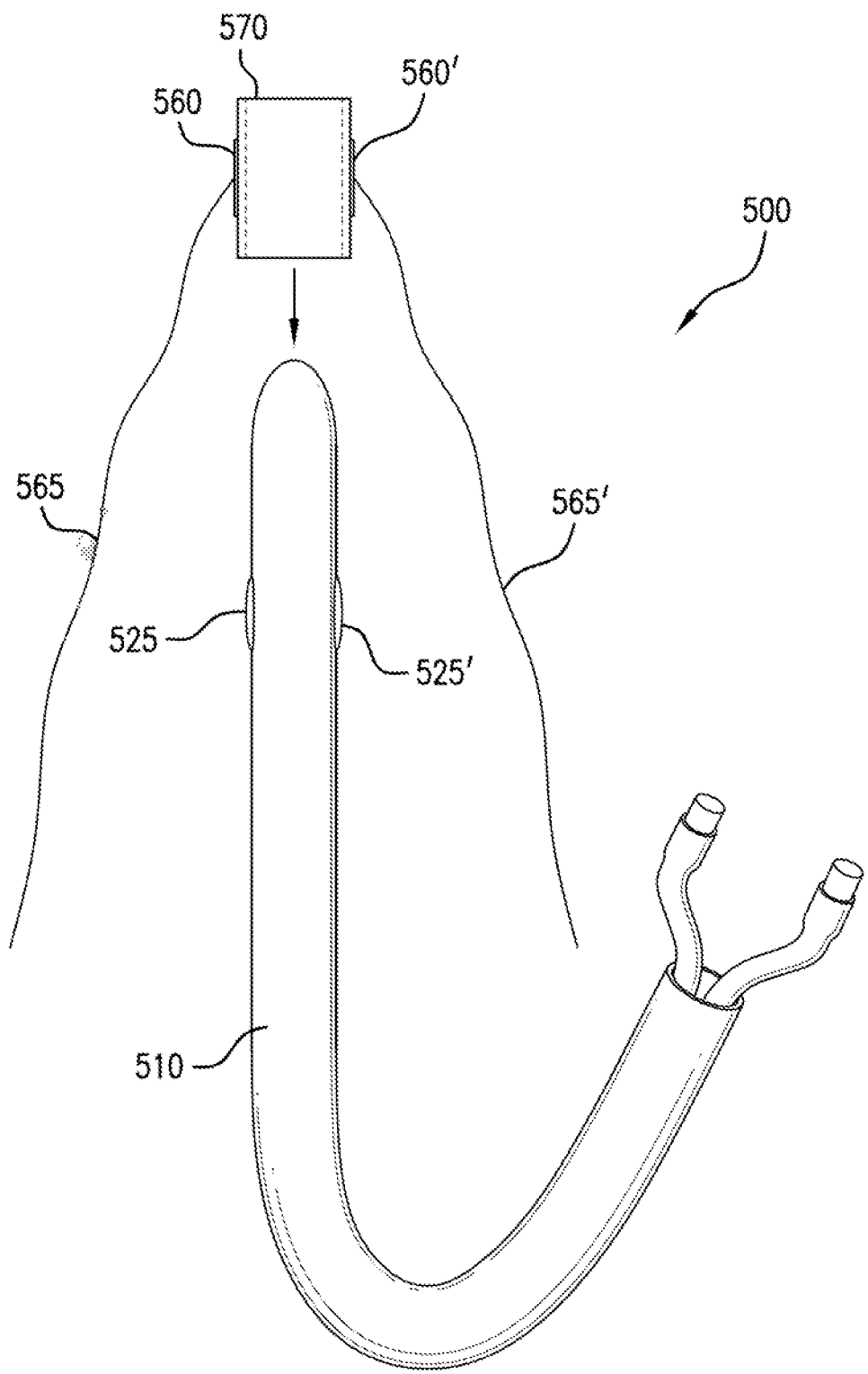
FIG. 5C is an illustration of a structure to mount electrodes to a pessary probe of FIG. 5A according to an embodiment.

There are various ways to attach the electrodes or other sensor equipment to the pessary 500. In one embodiment, the component is attached using an adhesive. In an alternative, and with reference to FIG. 5C, the electrodes can be formed on an elastic sleeve 570 which is configured to slide onto probe 510 and be placed along the probe to position the electrodes on the sleeve adjacent the inflatable portions 525, 525'. Sleeve 570 is shown in FIG. 5C as an open-ended cylinder. Alternatively one end could be closed, in full or part, so that the sleeve 570 can only be slid down on the probe 510 until the insertion end of the probe reaches the closed end of the cylinder. The dimensions of sleeve 570 and placement of electrodes can be selected so that when the sleeve is mounted on probe 510 to its full extent this places the electrodes in a known and desired position. The use of the open sleeve 570 can allow placement of the electrode(s), sensors, or other equipment on the sleeve 570 at a variety of locations along the length of the probe 510. Indicia can be provided on the probe, such as indicating a number of centimetres from the insertion end of the probe 510, to allow for placement of the sleeve 570 in a specific position on the probe 510 so as to result in the electrodes being placed at the desired location when the pessary 500 is in use.

While independently inflatable balloons 525, 525' are shown, in an alternative embodiment, the balloons 525, 525' can be connected to a common fluid conduit and be inflated simultaneously.

Figure 6A:
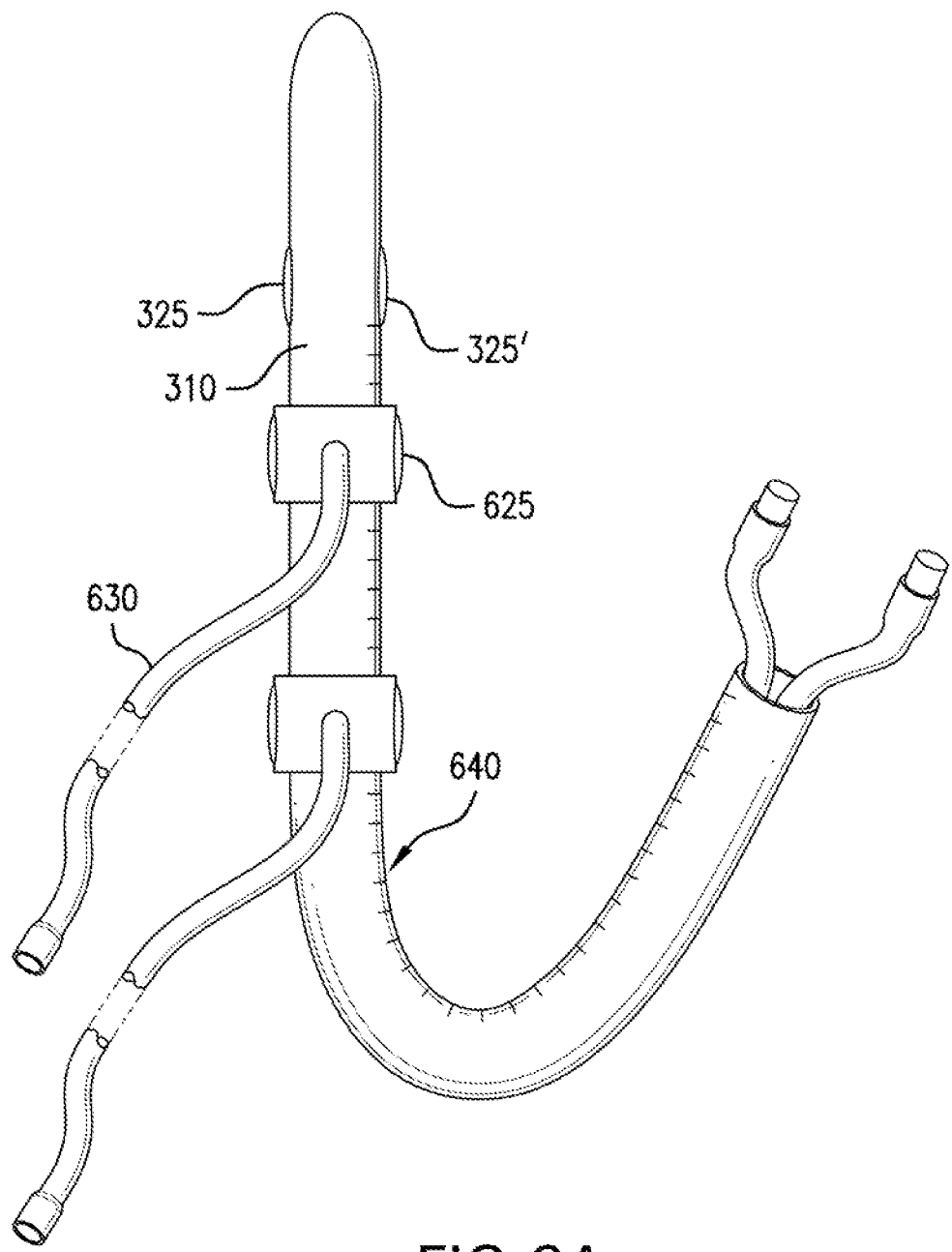
FIG. 6A is an illustration of the pessary of FIG. 3A with auxiliary inflatable balloon sleeves.

According to a further embodiment, and with reference to FIG. 6A, inflation of the inflatable portions 325, 325' firmly anchors the probe within the vaginal cavity. This allows the probe 310 to be used as a platform for additional supporting balloons. One or more auxiliary sleeves 625 can be placed onto the probe 310 at desired locations. Each sleeve 625 comprises an inflatable balloon 628 that can be inflated via a respective fluid conduit 630. In a typical embodiment, an auxiliary sleeve balloon 628 will inflate symmetrically into a 'donut' shape although other configurations are possible. The auxiliary sleeve balloon 628 can be a single chamber or can be bifurcated or otherwise configured so that only portions inflate.

The sleeve 625 is configured so it can be manually positioned along the probe 310, e.g., by sliding it up and down, but is sufficiently tight so that it will remain in a set position on the probe when the pessary is inserted for use. Inflation of the balloon 628 may further lock the sleeve 625 into position on the probe 310.

A given auxiliary sleeve 625 can be precisely placed within the vaginal cavity by positioning the sleeve on the probe 310 at a specific location, such as with reference to distance indicia 640. A sleeve 625 can be placed along the probe 310 to introduce an auxiliary balloon 628 to provide mechanical support for additional damaged or loose pelvic ligaments and to treat specific conditions. For example, support can be provided to the PUL, ATFP, CL, USL, and PB ligaments. As discussed above with respect to FIG. 2, weakness in these ligaments is believed to be a significant cause of organ prolapse such as bladder (cystocele), bowel (rectocele, descending perineal syndrome), and uterine/apical prolapse PLUS bladder/bowel/chronic pelvic pain symptoms.

Figure 6B:
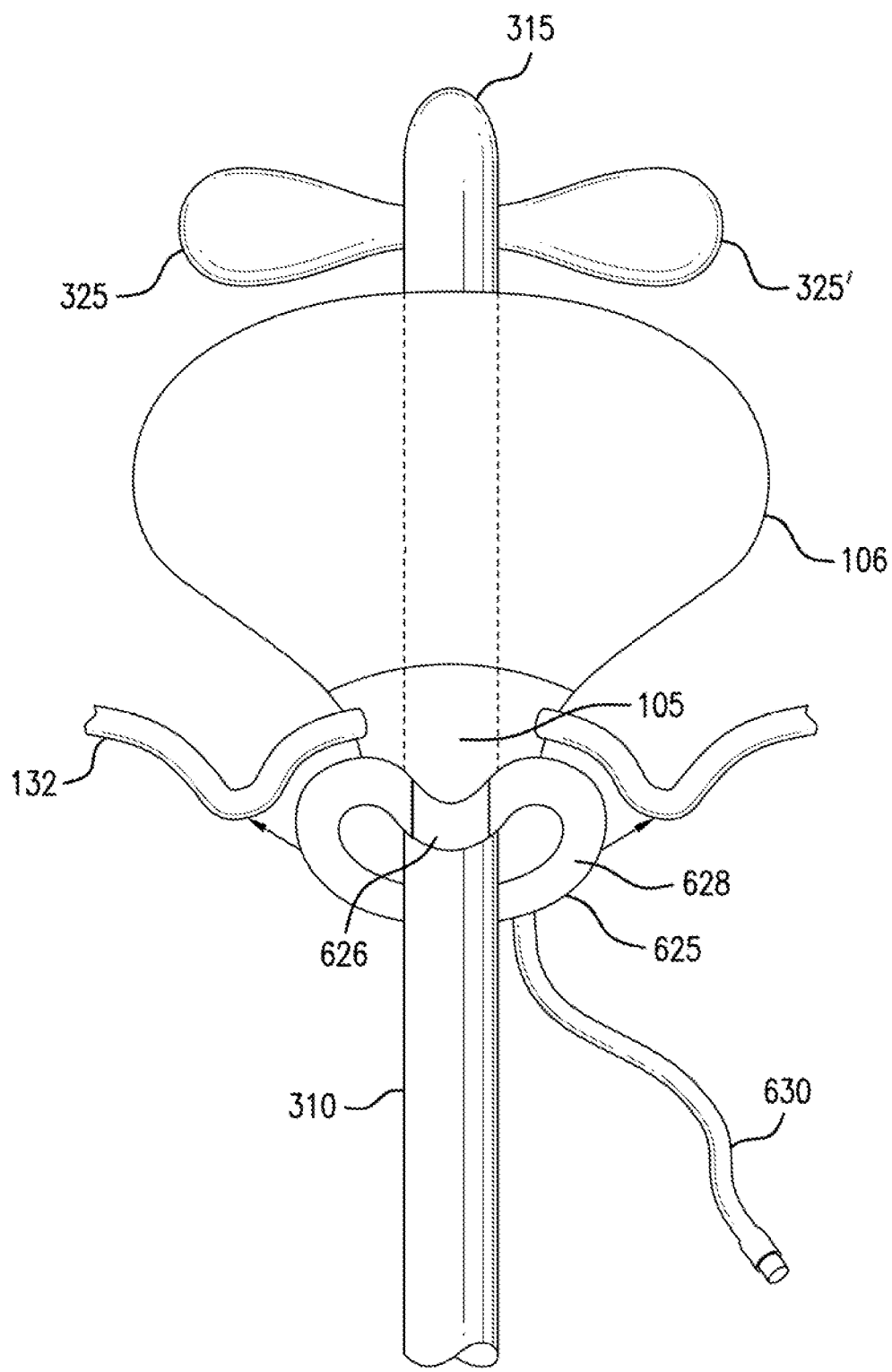
FIG. 6B is an illustration of a pessary with auxiliary inflatable balloon sleeve positioned to provide support of cardinal ligaments.

By way of example, and with reference to FIG. 6B, an auxiliary balloon sleeve 625 can be positioned on the probe 310 so that the auxiliary balloon 628 is precisely placed within the vaginal cavity immediately in front of the cervix 105 while the remainder of the probe 610 passes under the uterus 106 to rest in the posterior fornix of the vagina. The inflatable portions 325, 325' can provide support to the USL as discussed above. The auxiliary balloon 628, when expanded, can provide mechanical support to the cardinal ligaments 132 as they insert into the anterior cervical ring. Such an auxiliary balloon can be used for support of a "high cystocele" (transverse defect). In an embodiment, the auxiliary balloon 628 is configured so it does not encircle the cervix. In an embodiment with reference to FIG. 6B, where the auxiliary balloon 625 is used to provide support to the cardinal ligaments, the balloon can have a donut-like shape and be sufficiently large as to surround cervix and be able to be pushed onto the anterior lip of cervix. The sleeve 625 can have at least one solid section 626 which does not inflate and functions to prevents the auxiliary balloon 628 from inflating a substantial amount upwards but instead inflates primarily laterally to support the two ends of the dislocated cervical ligament,. In an embodiment two solid sections 626 are used and positioned on opposite sides of the probe so that the inflated balloon 628 when viewed axially will be generally shaped like the number 8.

Figure 6C:
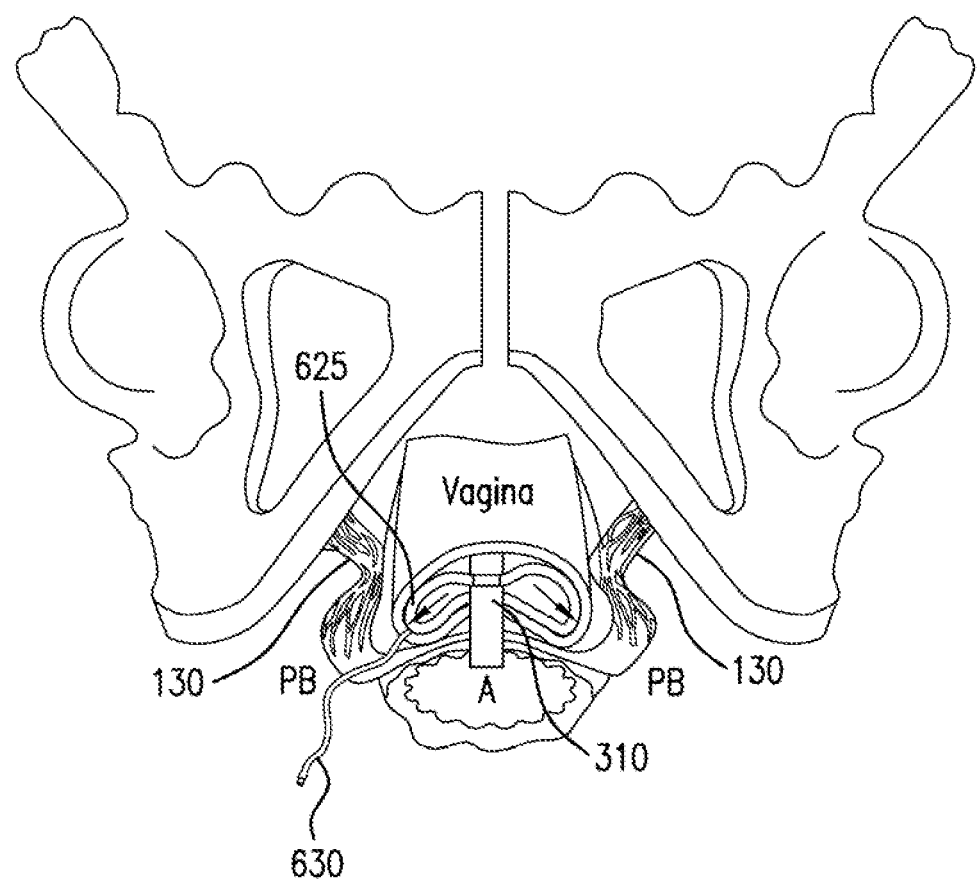
FIG. 6C is an illustration of a pessary with auxiliary inflatable supplementary balloon sleeve positioned to provide support of PB ligaments.

Similarly the auxiliary sleeve 625, or additional sleeves, can be placed further down on the probe to support the pubourethral ligament anteriorly (for SUI) and rectocele and perineal body posteriorly. The balloon 628 can be bifurcated, so one part goes up each side to support the ligamentous structure. This format has the advantage of not blocking the urethra for micturition or the bowel for defecation. FIG. 6C is an illustration of an auxiliary balloon sleeve 625 with a bifurcated balloon 628 of FIG. 6B and that is positioned to support the two deep PB ligaments 130.

Figure 7A:
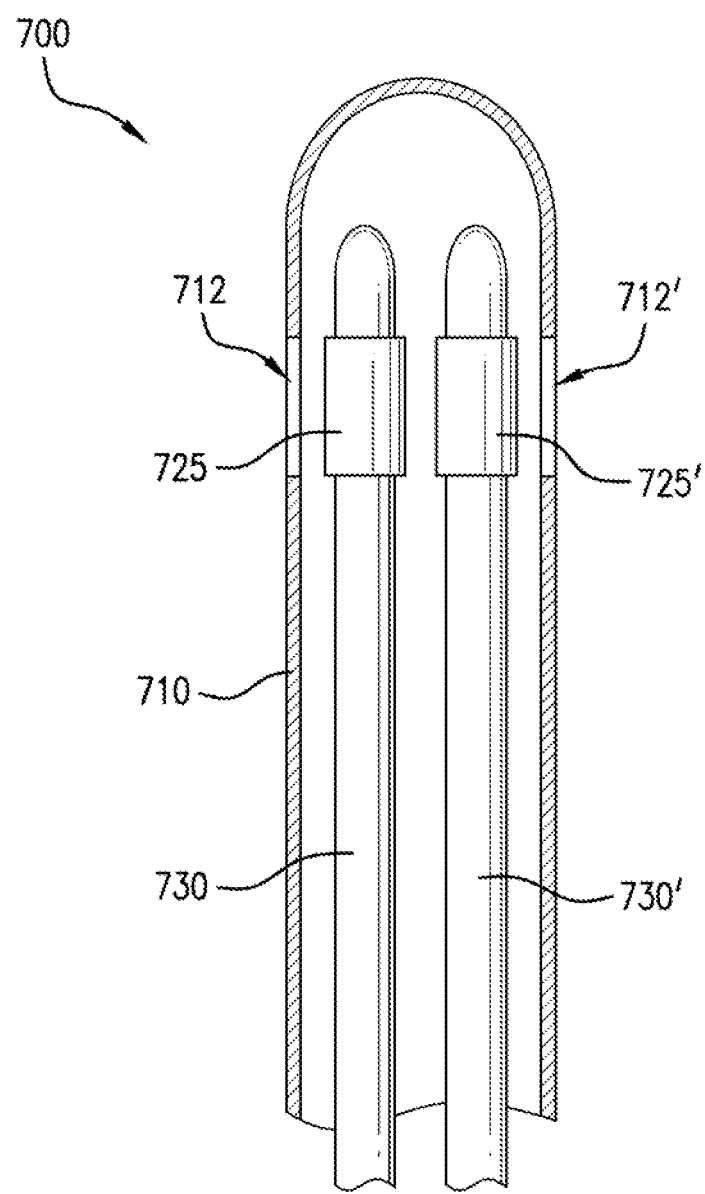
FIGS. 7A and 7B show a structure of a pessary with independently inflatable lateral balloons in an uninflated and inflated state respectively according to an embodiment.
Figure 7B:
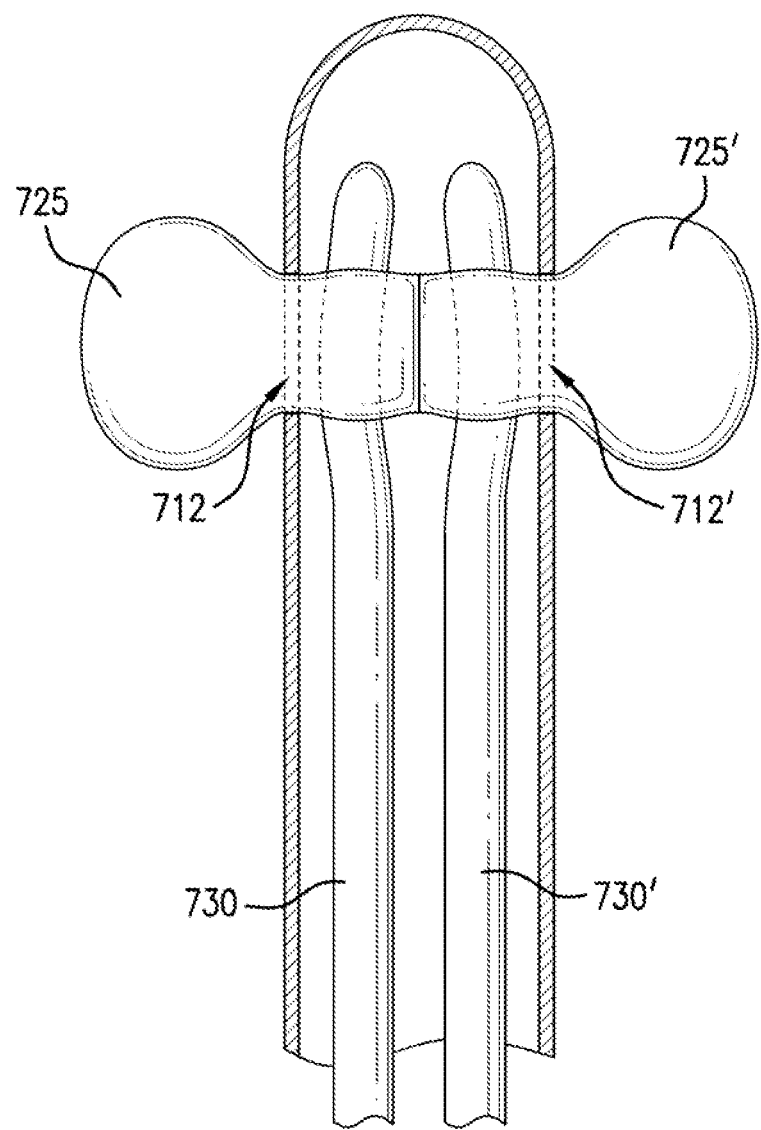

There are various ways in which a pessary with inflatable lateral balloons as disclosed herein can be structured. A particular embodiment of a pessary 700 is shown in FIGS. 7A and 7B in an uninflated and inflated state, respectively. In this configuration, a pair of fluid conduits, such as lumens 730, 730', is contained within an outer sleeve 710. Each fluid conduit 730, 730' has a respective inflatable balloon portion 725, 725' formed on it. The fluid conduits 730, 730' can be made of an elastic material and inflatable portions 725, 725' can be formed as a weakened or thin area of the respective conduit wall. Alternatively, the inflatable portions 725, 725' can be in the form of an inflatable donut which is affixed to and in fluid communication with the respective fluid conduit. In a particular embodiment, each fluid conduit 730, 730' and respective inflatable portion 725, 725' thereon is structured in a manner similar to that of a conventional balloon catheter, although the guidewire is not required.

The outer sleeve 710 has respective apertures 712, 712' which are aligned with the inflatable portions 725, 725'. During inflation, the balloon portions 725, 725' expand laterally outwards though the respective apertures 712, 712'. While the balloon portion 725, 725' of a single conduit 730, 730' if inflated outside of the pessary may tend to expand into a donut or ball shape, the expansion of each balloon portion 725, 725' in the pessary 700 is constrained by outer sleeve 710 and pressure from the other balloon portion and/or fluid conduit.

Figure 7C:
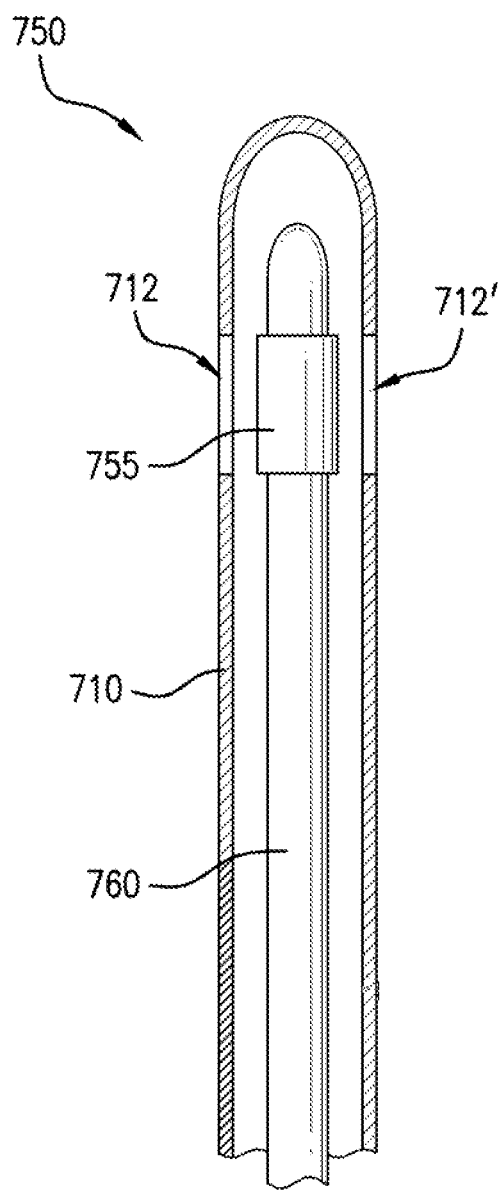
FIGS. 7C and 7D show an alternative embodiment of a pessary with inflatable lateral balloons in an uninflated and inflated state respectively.
Figure 7D:
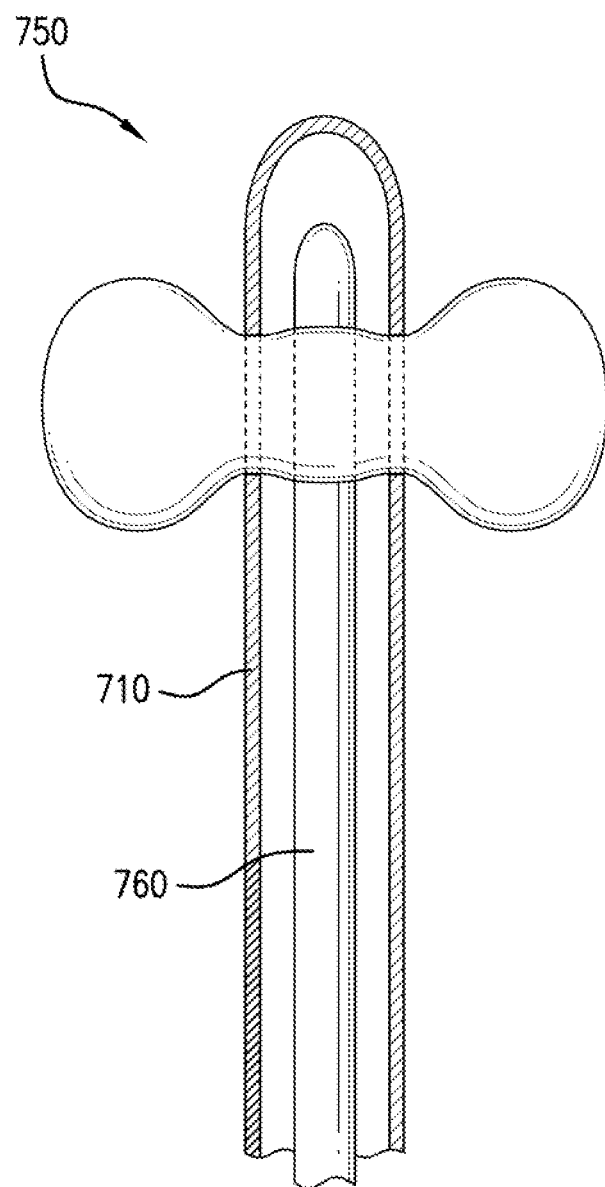

In an alternative embodiment where independent inflation is not required, a single balloon can be provided, such as would naturally inflate in a torus shape around a tube used for inflation. Apertures in the outer sleeve allow directed inflation in the desired axial locations while inflation in other areas is constrained. Such an embodiment is shown in FIGS. 7C and 7D. Pessary 750 has a balloon portion 755 inflatable via fluid conduit 760. Outer sleeve 710 with apertures 712, 712' is positioned to align the apertures with the balloon 755 and thereby define areas of the probe 750 in which the balloon 755 can expand laterally.

Figure 8A:
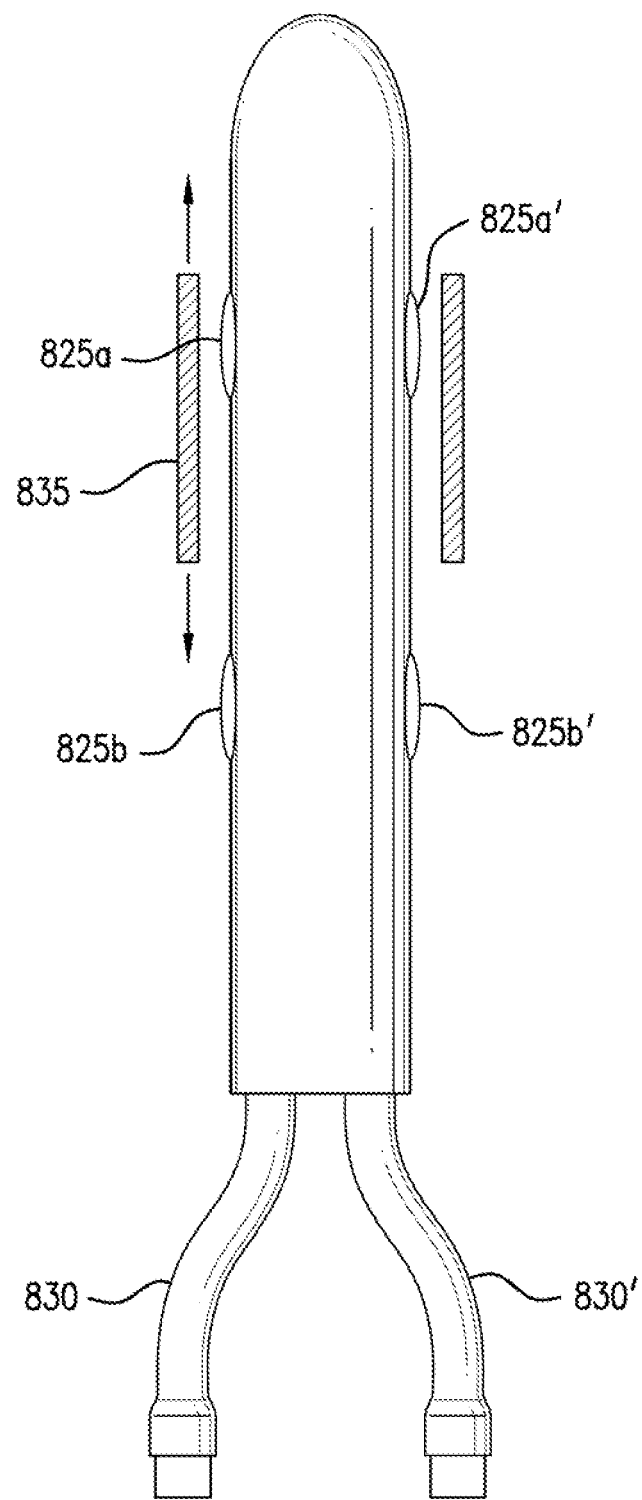
FIGS. 8A-8D and FIG. 9 show pessary structures configured to allow customization of the lateral balloon positioning according to various embodiments.

FIG. 8A shows a further embodiment 800 in which the position of the laterally inflatable portions relative to the insertion end can be selected from two or more predefined positions to allow for custom fitting to a given patient. In this configuration, each fluid conduit 830, 830' can operate as a manifold to feed multiple inflatable portions along the length of the probe 810. For example, conduit 830 feeds inflatable portions 825a and 825b located a distance D1 and D2 from the insertion end 815. Likewise, conduit 830' feeds inflatable portions 825a' and 825b'. An outer sleeve 835 can be positioned along the longitudinal axis of the probe so that it covers one pair of inflatable portions, 825a, 825a' or 825b, 825b' while the other pair is left uncovered. During an inflation action, the uncovered pair of inflatable portions will inflate while the sleeve 835 constrains inflation of the covered pair. Multiple sleeves can be used on the probe to selectively block inflation of additional inflatable portions on the probe if present.

Figure 8B:
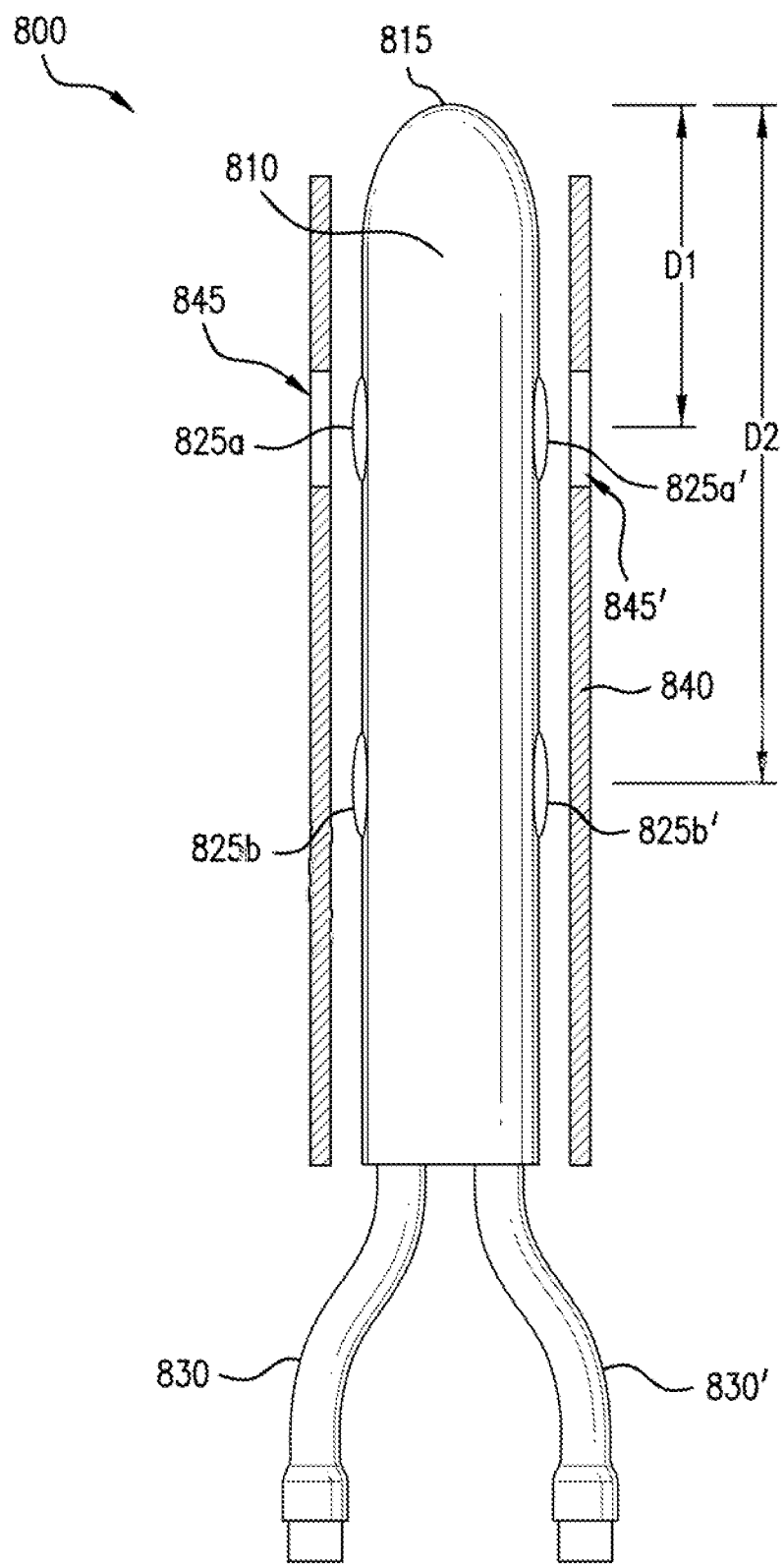

FIG. 8B is a variation of the embodiment of FIG. 8A in which an outer sleeve 840 is configured to be slipped over the probe 810 and has one or more apertures, such as apertures 845, 845'. The sleeve 840 can be positioned on the probe 810 so that each aperture 845, 845' exposes a selected inflatable portion, such as inflatable portions 825a, 825a' while other inflatable portions are covered by the sleeve. When fluid is introduced into the conduits 830, 830', the inflatable portions 825a, 825a' exposed by the apertures 845, 845' can inflate and expand laterally beyond the outer sleeve 840 while other inflatable portions 825b, 825b' are restricted by the outer sleeve 840 and confined within the sleeve 840. Depending on the overall geometry of the pessary 800, a single outer sleeve 840 may be positionable along the probe 810 to expose one pair 825a, 825a' or the other pair 825b, 825b' of inflatable portions. Alternatively, the pessary 800 can be provided with multiple outer sleeves 840 each with apertures positioned to align with a selected pair of inflatable portions. The sleeve 840 and aperture placement thereon may also be configured so that the sleeve orientation can be reversed so that with the sleeve in the same position on the probe, the exposed inflatable portions are determined by whether a first end of the sleeve is closest to the insertion end of the probe or closest to the distal end of the probe.

Figure 8C:
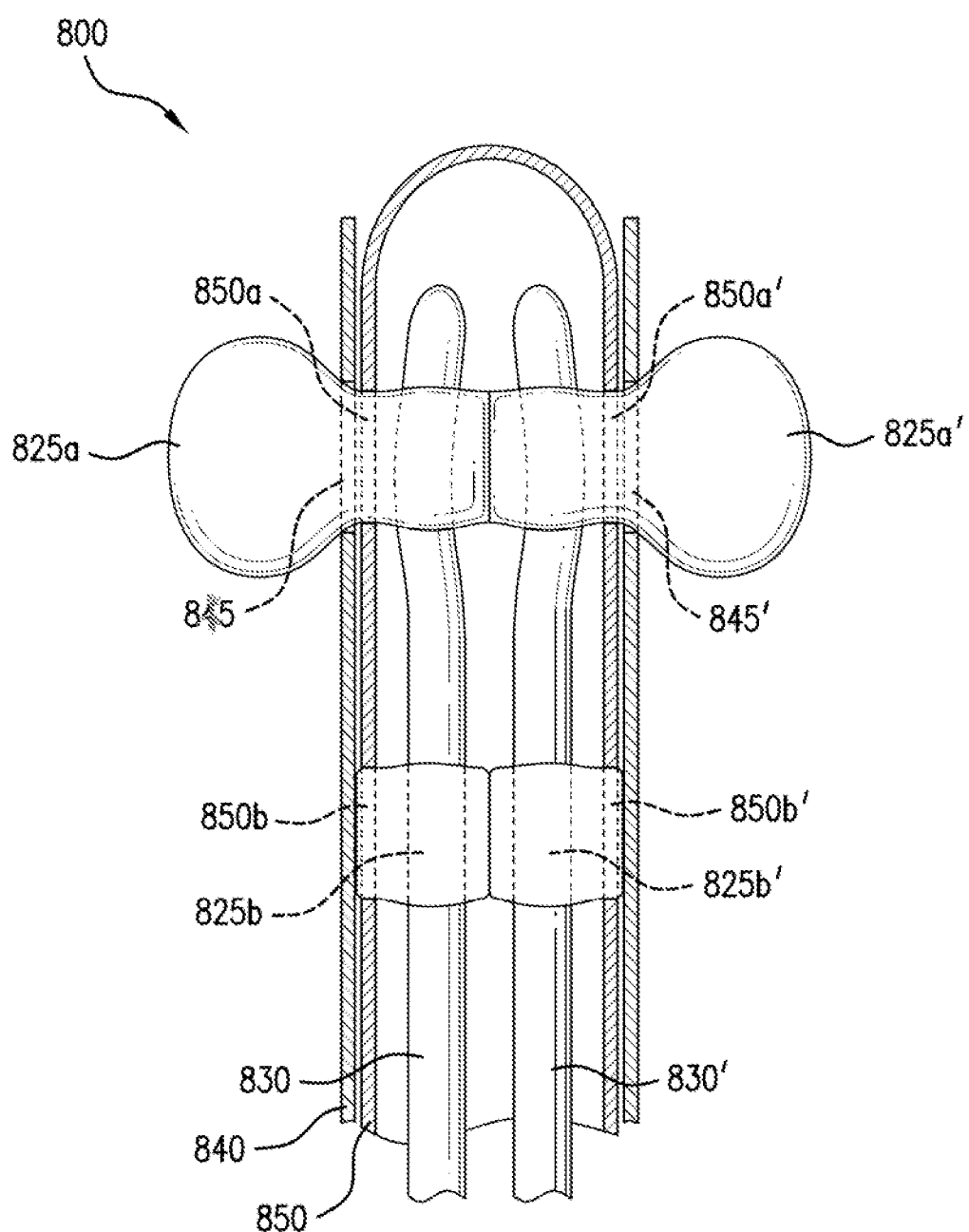

FIG. 8C is a variation of FIG. 8B in which the inflatable portions 825a, 825a', 825b, 825b' are formed along the length of a respective fluid conduit 830, 830'. Analogous to FIG. 8B, the probe 850 has apertures 850a, 850a', 850b, 850b' which expose the respective inflatable portions allowing for lateral expansion. Outer sleeve 840 is positioned along the length of the probe 850 to place the apertures 845, 845' in the outer sleeve 840 adjacent the inflatable portion positioned in the desired location. When fluid is introduced into a given fluid conduit, such as conduit 830, all of the inflatable portions along its length will be subject to inflation. However, only the inflatable portions adjacent the respective aperture in the outer sleeve 840 can expand laterally outwards from the probe while inflation of the other inflatable portions is restricted by the outer sleeve.

Figure 8D:
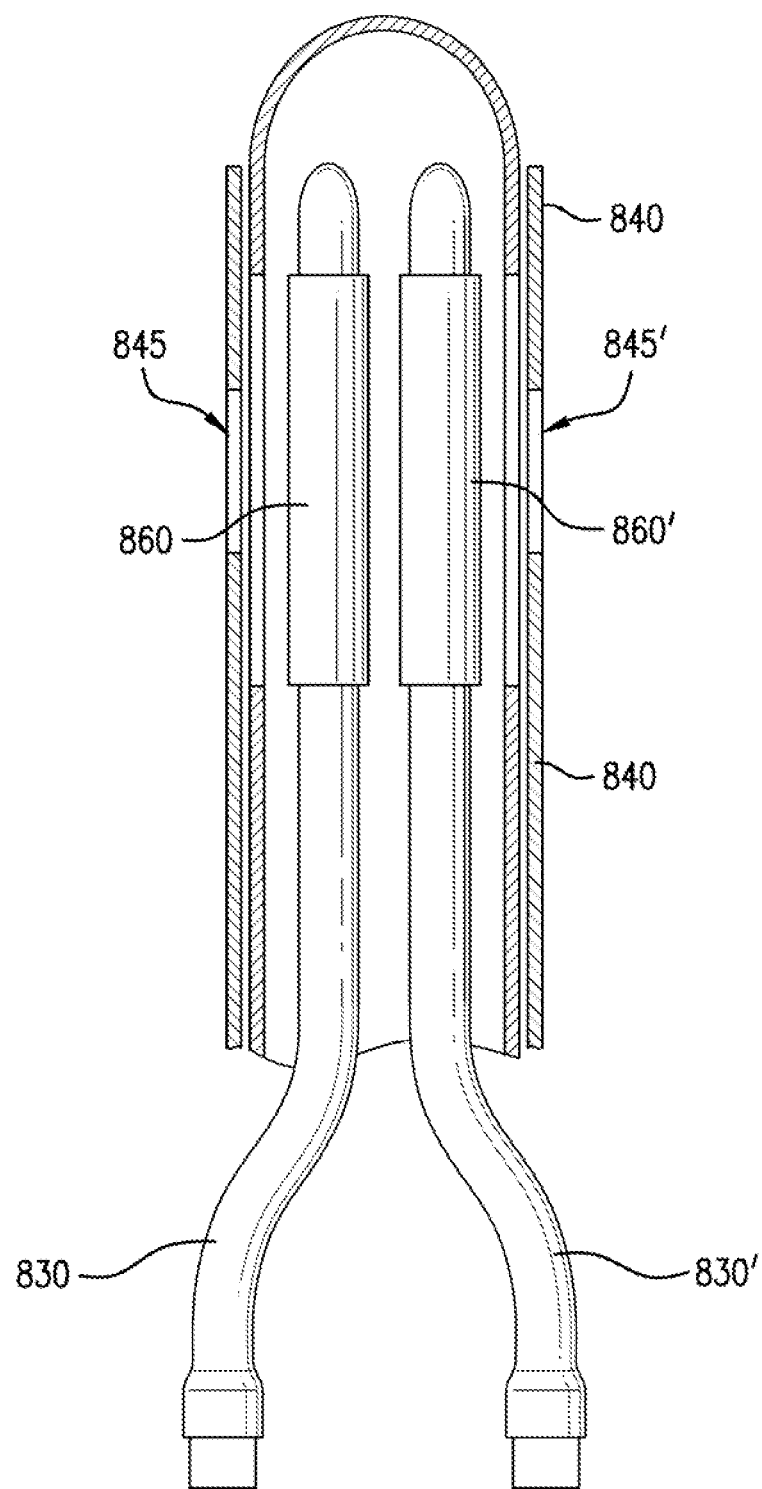

Yet a further variation of this embodiment is shown in FIG. 8D. In this configuration, rather than having multiple separate inflatable portions along a length of a fluid conduit 830, 830', the fluid conduit has an elongated inflatable portion instead, such as elongated inflatable portions 860, 860'. The position of lateral inflation relative to the insertion end is governed by the position of the external sleeve 840 and the apertures 845, 845' therein.

Figure 9:
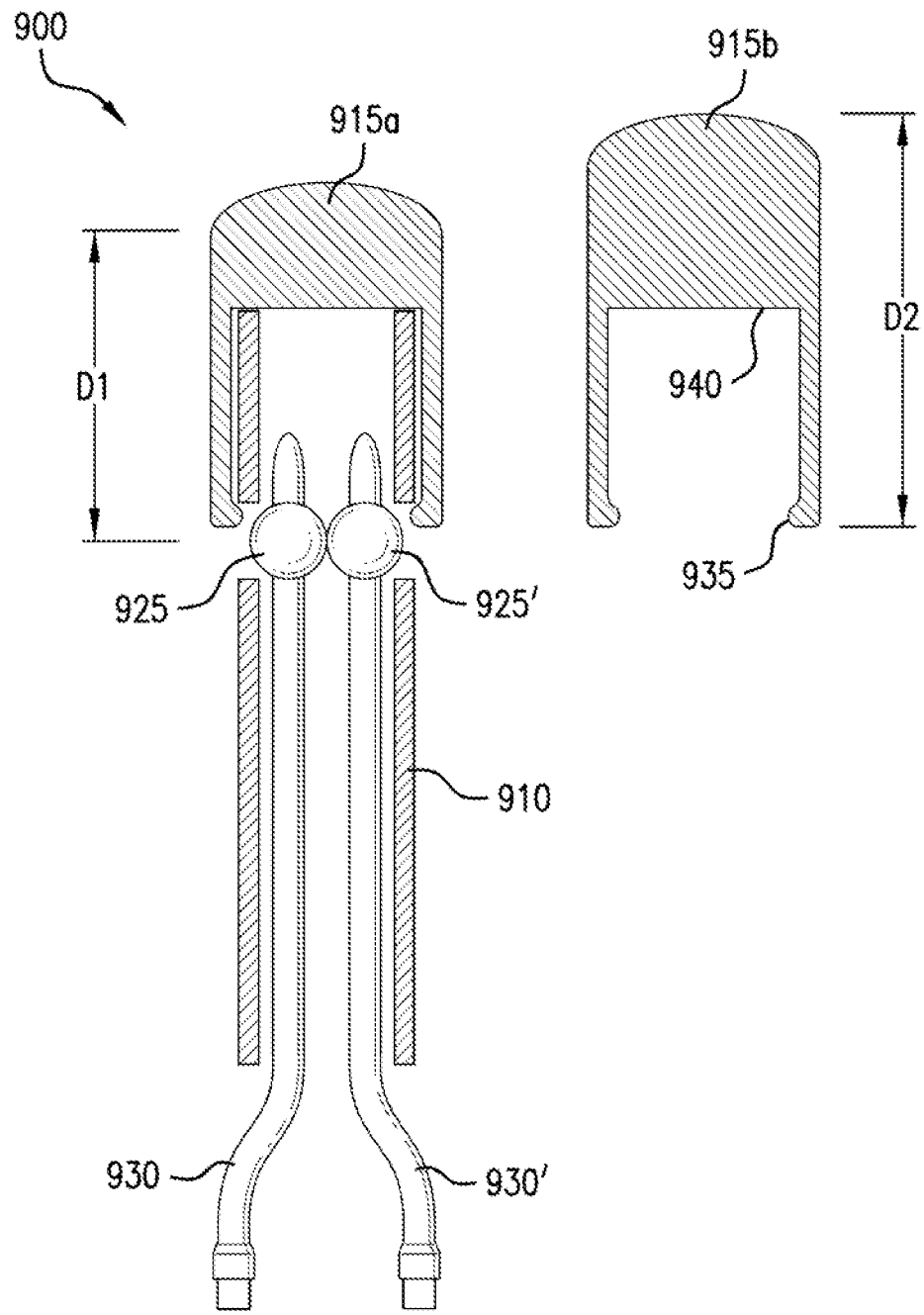

In a further alternative and with reference to FIG. 9, pessary 900 has a main probe body 910 with inflatable portions 925, 925' inflatable through respective fluid conduits 930, 930'. Inflatable portions can be integral to the probe body 910 or formed on internal lumens or other conduits and positioned adjacent apertures in the probe body 910. Differently sized end-caps, such as end caps 915a, 915b can be provided to allow selection of the desired distance between the inflatable portions 925, 925' and the insertion end of the pessary 900 at the desired position when the pessary 900 is fully inserted. For example, use of end cap 915a positions the inflatable portions 925, 925' a distance D1 from the insertion end and use of end cap 915b positions them a distance D2 from the insertion end.

The end caps 915a, 915b can be mountable to the probe body 910 by a variety of mechanisms. For example, end caps can be somewhat elastic and mounted using a friction fit to the probe body 910. Mechanical retaining structures, such as detents 935 configured to engage the apertures in the probe body 910 or other structures on the probe body can be used to prevent removal. Various other retention mechanisms known to those of skill in the art can be used. In a further variation, the pessary system is configured so that the mounting position of a single end cap along the probe body is selectable to thereby allow adjustment of the distance between the insertion end and the inflatable portions 925, 925'. For example, the end cap and probe body can be configured so the end cap will snap fit into two or more different positions. Other mechanisms known to those of skill in the art that allow an adjustable mounting position can also be used.

As discussed with other embodiments, if independent lateral inflation of the balloons is not required, the dual balloon/inflation conduit structure of FIGS. 8A-8D and FIG. 9 can be replaced with a single balloon and inflation conduit. According to a further embodiment, various methods for providing pelvic floor ligament support treating prolapse and descending perineal syndrome), uterine/apical prolapse, bladder/bowel/chronic pelvic pain symptoms, and other conditions are provided.

In one treatment a pessary, such as pessary 300 as in FIG. 3A, is provided and inserted into the vagina, such as by a physician or a user, to place the inflatable portions of the pessary behind the cervix. This may entail inserting the pessary its fullest extent or inserting it less than the full amount. If inserted less than the full amount the insertion measurement can be initially be recorded during a fitting by a position to allow for subsequent self-insertion by the patient the same amount. (The insertion measurement distance could also be recorded and communicated to the patient even if full insertion is desired.)

The balloons are then independently inflated an amount sufficient to bring each balloon below the respective USL. The proper amount of inflation can be determined by the treating physician, for example based on the degree of pain relief or reduction in urgency provided as the balloons are inflated. Alternatively if there is significant prolapse, an appropriate amount of inflation can be determined by inflating and testing if the balloon is holding fast and when the fit is secure, the amount of fluid required for each side can be noted. The amount of inflation required can also be determined by the patient based on the degree of pain relief or reduction in urgency provided as the balloons are inflated.

A measure of inflation volume is also recorded and can be communicated to or recorded by the patient so that the patient can subsequently perform a self-insertion method of treatment and can inflate each balloon the appropriate amount. For example, fluid can be introduced by a syringe or other mechanism that has indicia providing a measurement of the volume of fluid introduced. The indicia can be used to measure the fluid amount introduced by the physician and used by the patient select the volume of fluid used to inflate the respective inflatable portion 325, 325'.

A single syringe can be used sequentially to introduce a predefined volume of fluid into one conduit 330 and then then other conduit 330' to inflate the inflatable portions 325, 325' in turn. Alternatively, two syringes can be connected to respective conduits 330, 335' to allow simultaneous inflation. Instead of an initial fluid injection by volume, air can be injected until a predefined pressure is reached, at which point the volume of air injected can be recorded for later use. The two syringes can be ganged together or physically separate from each other. In a ganged configuration, the syringe plungers can be separately depressible or they can be connected to each other so they must be depressed simultaneously.

In a further configuration, adjustable constant volume syringes can be provided so that the total amount of fluid injected when each plunger is depressed the full amount can be set to the desired volume. The syringes can be configured by the doctor during the initially pessary fitting session to set the appropriate fluid injection volume. The total injection volume can be configured, e.g., by adjusting the length of the plunger stem that can be inserted into the syringe. For example, the plunger tips can be attached to the stems by a threaded or slidable rod. Suitable adjustment mechanisms for constant volume syringes are known to those of skill in the art.

Figure 11:
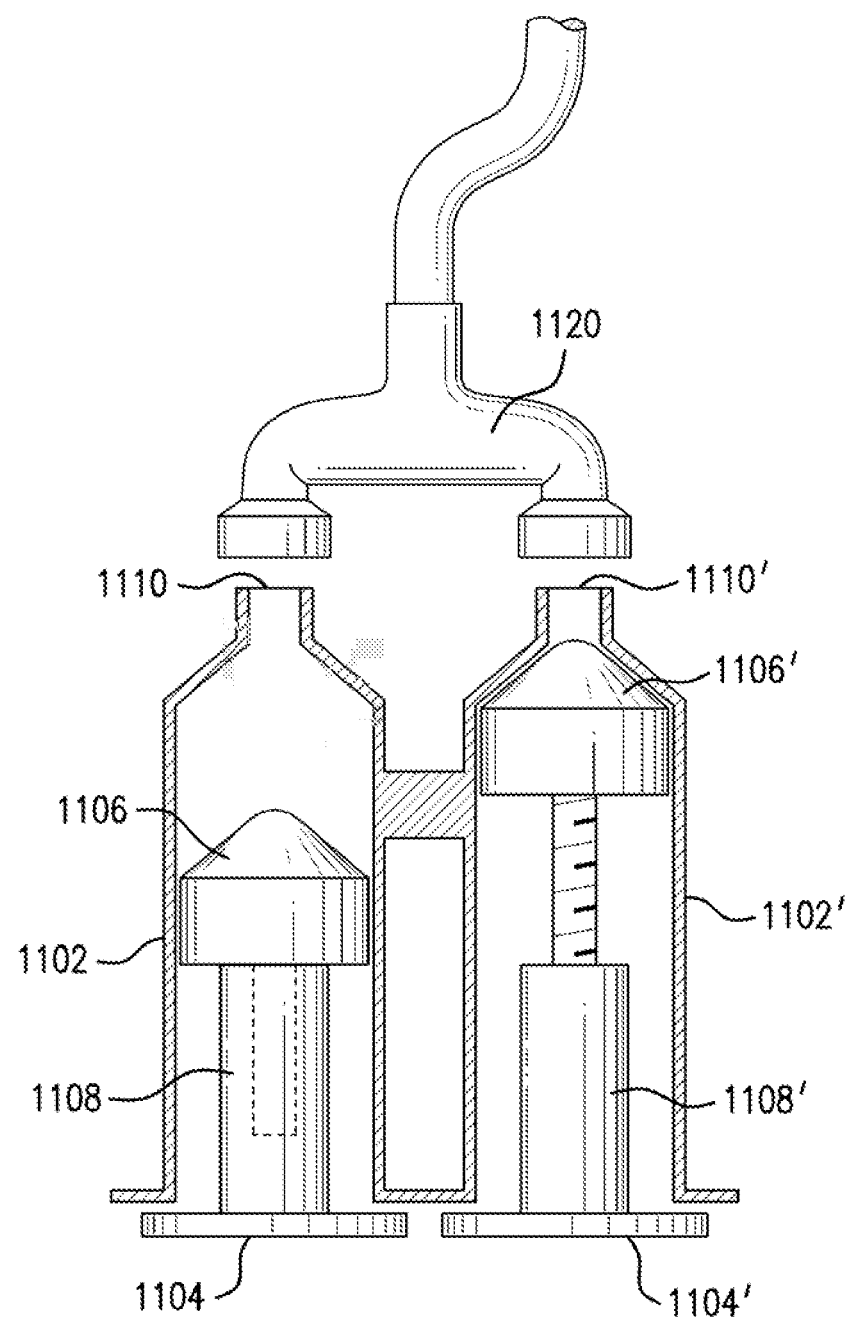
FIG. 11 is an illustration of an adjustable syringe mechanism for use in inflating a dual balloon pessary as disclosed herein.

In a particular embodiment, shown in FIG. 11, a pair of adjustable constant volume syringes 1102, 1102' are provided, each having a plunger 1104, 1104' with a respective plunger tip 1106, 1106' and adjustable length stem 1108, 1008'. The two syringes 1102, 1102' can be physically connected to each other and configured so the ends 1110, 1110' of the plungers can both be connected to an injection coupler 1120 which puts each syringe in fluid connection with a respective inflation conduit. The conduit coupler and syringes can be configured so that each syringe only be fitted to the injection port of the coupler 1120 for the pessary balloon for which the syringe volume is set.

Where the pessary is configured as in FIGS. 8A and 8B, the method of treatment can further include the step of selecting from a plurality of apertures at different varying locations along the probe one or more inflatable apertures at particular distances from the insertion end of the probe from by placing an outer sleeve 840 with apertures 845, 845' onto the probe 810 and positioning it so that the apertures expose the selected inflatable portions while the sleeve restricts inflation of other such portions. The method can include the step of receiving the pessary with a plurality of outer sleeves each of which has apertures in different locations and selecting a particular sleeve from a plurality of sleeves. The method can include the step of receiving the pessary and an outer sleeve, forming apertures in the sleeve at a selected location on the sleeve, and then placing the sleeve on the pessary so the apertures expose selected inflatable portions.

Where the pessary is configured as in FIGS. 8A and 8B, the method of treatment can further include the step of selecting an outer sleeve 840 with apertures 845, 845' therein and positioning the sleeve onto the probe so that the apertures are positioned a particular distance from the insertion end so as to adjust the axial position of where the inflatable portions will laterally expand when inflated.

Where the pessary is configured as in FIG. 9, the method of treatment can further include the step of adjusting the distance between the inflatable portions and the insertion end of the probe by placing a selected endcap onto the pessary probe body 910. The method can include receiving the pessary with a plurality of differently sized end caps and selecting the particular end cap from them.

In a further method of treatment, an auxiliary balloon sleeve is fitted to the pessary, such as by the physician. The sleeve is positioned on the pessary so that when the pessary is inserted the specified amount (such as fully or a defined length as discussed above), the balloon on the sleeve will be positioned to provide auxiliary ligament support.

In a particular method for positioning the sleeve, the sleeve is configured to fit loosely on the pessary probe 310. A firm anchoring of the apex of the probe in the vagina is obtained by blowing up the two posterior balloons on the probe. Next, the sleeve is slid along the probe 310 to the precise position required to support the damaged ligament. Alternatively, where the sleeve is more tightly fitting on the pessary, the sleeve can be prepositioned on the pessary prior to insertion. The balloon on the sleeve is then inflated. The distance from a fixed marker on the pessary probe to the auxiliary balloon can be noted. The amount of fluid required can also be noted.

In a particular treatment method, the positioning is determined so that a sleeve with auxiliary balloon is positioned within the vaginal cavity immediately in front of the cervix 132. After the pessary is inserted, the primary balloons are independently inflated to provide support for the USL and the supplemental balloon is inflated to provide supplemental support to the CL. When use of the pessary is no longer desired, the balloons are deflated and the pessary removed from the vagina.

In variations of a method of treatment, the auxiliary balloon is positioned on the probe to provide mechanical support for back, middle, or front ligaments for treatment of various conditions, such as those detailed in FIG. 2. Thus, in various examples, (i) in a method for treatment of rectocoele, uterine/apical prolapse, abnormal emptying, frequency and urgency, nocturia, faecal incontinence, obstructed defecation, or pelvic pain, the auxiliary balloon is positioned to provide support for back ligaments (such as the USL and PB); (ii) in a method for treatment of cystocoele, abnormal emptying, frequency and urgency, and tethered vagina, the auxiliary balloon is positioned to provide support for middle ligaments (such as the ATFP and CL); and (iii) in a method for treatment of stress incontinence, frequency and urgency, and faecal incontinence, the auxiliary balloon is positioned to provide support for front ligaments (such as the PUL) and posteriorly for rectocele and descending perineal syndrome. In a variation of the treatment method more than one auxiliary balloon can be used to provide support for multiple different ligaments.

According to an additional embodiment, a method of performing electromyography (EMG) assessment and/or muscle stimulation comprises inserting (e.g., by a physician) a pessary, such as pessary 500 as in FIG. 5A, into the vagina to place the inflatable portions of the pessary behind the cervix. This may entail inserting the pessary its fullest extent or inserting it less than the full amount. These balloons are independently inflated an amount sufficient to hold the pessary in position. Sensors mounted on the pessary detect internal electrical signals which are carried by wires to an EMG sensing system that can record the signals, translate these signals into graphs, sounds or numerical values. The output values can be interpreted by a specialist or for use in while performing other procedures.

The EMG sensors can be mounted on the inflatable portions 525, 525' of the pessary and the step of inflation of these portions performed to position the EMG electrodes in a desired location, such as directly over the pelvic muscles on each side of the vagina. The method can include the step of receiving the pessary and then attaching EMG sensors the pessary prior to the procedure, such as by adhesive or via a sliding sleeve 560. Other steps include positioning one or more EMG sensors elsewhere on the pessary, in addition to or as an alternative to EMB sensors associated with inflatable portions 525, 525'. Such sensors can be placed on the body of the probe or on sleeves fitted over the probe, and could be provided with or attached to auxiliary balloon sleeves as discussed, e.g., with respect to FIG. 6A.

In a further method, in addition to or as an alternative to EMG sensors, muscle stimulation electrodes are attached to the pessary in a manner similar to that addressed above for EMG sensors. The pessary is inserted, inflated to secure the pessary in place and, where the electrodes are on an inflatable portion the position of the electrodes is adjusted as may be required. Electrical signals are then applied to the electrode to stimulate the muscles adjacent the electrodes. In a particular method, the muscle stimulation electrodes are attached to or mounted over the inflatable portions 525, 525' and inflation is used to position the electrodes over the pelvic muscles on each side, such as the pubococcygeus muscles, and then electrical signals are applied to stimulate these muscles. Other steps include positioning one or more electrodes for muscle stimulation elsewhere on the pessary, in addition to or as an alternative muscle stimulation electrodes associated with inflatable portions 525, 525'. Such sensors can be placed on the body of the probe or on sleeves fitted over the probe, and could be provide with or attached to auxiliary balloon sleeves as discussed, e.g., with respect to FIG. 6A.

It should be appreciated that the method can include both EMG sensing and muscle stimulation and that these activities can be performed in sequence or at the same time, and that they can use the same or different electrodes.

Various aspects, embodiments, and examples of pessaries and methods for use have been disclosed and described herein. Modifications, additions and alterations may be made by one skilled in the art without departing from the spirit and scope of the inventions as defined in the appended claims.

The invention claimed is:

1. A pessary system for providing pelvic floor ligament support comprising:
    an elongated probe extending along a longitudinal axis and configured for insertion through a vagina and into a vaginal cavity of a patient, the probe having an insertion end and a distal end;
    a sleeve having a body extending along the longitudinal axis with a forward part of the sleeve closest to the insertion end and respective first and second side apertures in the body of the sleeve and distal to the forward part of the sleeve, a first inflatable portion a first distance from the insertion end and adjacent the first side aperture;
a second inflatable portion substantially the first distance from the insertion end and adjacent the second side aperture;
at least one conduit in fluid communication with the first inflatable portion and the second inflatable portion, the first and second inflatable portions being inflatable using fluid introduced through the at least one conduit;
each of the at least one conduit extending from the probe and terminating in a respective coupler adjacent the distal end of the probe;
wherein the first inflatable portion is positioned inward from the first aperture relative to the longitudinal axis and the second inflatable portion is positioned inward relative to the longitudinal axis from the second aperture, such that inflation of the first and second inflatable portions is constrained by the sleeve and the first inflatable portion when inflated expands laterally outwards away from the longitudinal axis through the first aperture and into a first radial sector and the second inflatable portion when inflated expands laterally outwards away from the longitudinal axis through the second aperture and into a second radial sector.

2. The pessary of claim 1, the probe having a forward section adjacent the insertion end, a rear section adjacent the distal end, and wherein at least a portion of the rear section of the probe is sufficiently flexible so that when the forward section is inserted into the vaginal cavity of the patient to a treatment position a portion of the rear section remaining external to the vagina is positionable to be held inside underwear being worn by the patient.

3. The pessary of claim 1, wherein the at least one conduit comprises a first conduit for inflation of the first inflatable portion and a second conduit for inflation of the second inflatable portion independently from inflation of the first inflatable portion.

4. The pessary of claim 3, wherein the first inflatable portion is a weakened area of the first conduit and the second inflatable portion is a weakened area of the second conduit.

5. The pessary of claim 1, wherein the sleeve is an outer sleeve.

6. The pessary of claim 1, a position of the sleeve along the longitudinal axis of the probe being adjustable, wherein adjusting the position of the sleeve changes the first distance.

7. The pessary of claim 1, wherein a width of the probe perpendicular to the longitudinal axis along a portion of the pessary configured for insertion into the vagina is between 1 cm and 2 cm.

8. The pessary of claim 7, wherein the width is between 1.3 cm and 1.7 cm.

9. The pessary of claim 8, wherein the width is between 1.5 cm and 1.6 cm.

10. A method for providing support to pelvic floor ligaments of a patient having a vaginal cavity with an apex, the method comprising the steps of:
providing a pessary comprising an elongated probe configured for insertion into a vagina, the probe having a length L1 along a longitudinal axis from an insertion end to a distal end, and having a first balloon located a first distance from the insertion end, the first balloon inflatable through a first conduit;
inserting the probe into the vaginal cavity of the patient;
manipulating the pessary to place the pessary at a treatment position within a vaginal cavity, wherein when the pessary is positioned at the treatment position, a rear section of the probe remains external to the vagina and a forward section of the probe is within the vaginal cavity;
inflating the first balloon when the pessary is at the treatment position; and
cutting a portion of the rear section of the probe at a cut-point and removing the cut portion from the pessary to create a customized pessary probe having a length L2 along the longitudinal axis from the insertion end to a new distal end defined by the cut point and wherein L2 is less than L1.

11. The method of claim 10,
the pessary having a second balloon located at substantially the first distance from the insertion end, the first and second balloons inflatable into respective non-overlapping first and second radial sectors;
the treatment position being a position wherein the first and second balloons are within an apex of the vaginal cavity and oriented so that when the first and second balloons are inflated, each balloon will provide ligament support to a respective pelvic floor ligament, wherein when the patient is one with a cervix, the first and second balloons are positioned behind the cervix;
the step of inflating the first balloon comprising inflating the first balloon to provide ligament support on a first lateral side of the patient by the first balloon;
the method further comprising the step of inflating the second balloon when the pessary is at the treatment position to provide ligament support on a second lateral side of the patient by the second balloon.

12. The method of claim 11, wherein the respective pelvic floor ligaments are a first uterosacral ligament (first USL) and a second uterosacral ligament (second USL);
the step of inflating the first balloon comprising inflating the first balloon to position the first balloon below the first USL on the first lateral side of the patient to support the first USL; and
the step of inflating the second balloon comprising inflating the second balloon to position the second balloon below the second USL on the second lateral side of the patient to support the second USL.

13. The method of claim 11, the pessary further comprising an auxiliary balloon positioned on the probe an auxiliary second distance from the insertion end that is further than the first distance, the auxiliary balloon inflatable independently of the first and second balloons;
the treatment position putting the auxiliary balloon within the vaginal cavity distal to the apex;
the method further comprising the step of inflating the auxiliary balloon, wherein the inflated auxiliary balloon provides auxiliary ligament support.

14. The method of claim 11, wherein the first and second balloons are independently inflatable, the method further comprising the steps of, after the step of inserting the pessary into a vagina:
determining a first volume of fluid needed to inflate the first balloon a first amount to provide the ligament support on the first lateral side of the patient;
determining a second volume of fluid needed to inflate the second balloon a second amount to provide the ligament support on the second lateral side of the patient;
recording the first and second volumes; and removing the probe from the vaginal cavity.

15. The method of claim 14, further comprising the steps of:
  inserting the customized pessary probe into the vaginal cavity of the patient substantially to the treatment position;
  inflating the first balloon with the first volume of fluid to provide the ligament support on the first lateral side of the patient; and
  inflating the second balloon with the second volume of fluid to provide the ligament support on the second lateral side of the patient.

16. The method of claim 10, wherein during the step of manipulating, when the pessary is positioned at the treatment position an axial length of the rear portion of the probe is greater than an axial length of the forward portion of the probe.

17. The method of claim 10, wherein the removed portion of the rear section comprises the entire rear section, wherein when the customized pessary probe is subsequently inserted into the vagina and placed at the treatment position, the entire customized pessary probe is within the vagina.

18. The method of claim 10, the step of cutting the pessary further comprises cutting the first conduit; the method further comprising attaching a coupler to a cut end of the first conduit.

19. The method of claim 10, wherein after the step of cutting the pessary, the first conduit extends past the new distal end of the customized pessary probe; and
  wherein when the customized pessary probe is inserted into the vagina and placed at the treatment position, the first conduit remains external to the vagina and can be used to subsequently remove the customized pessary from the vagina.

* * * * *